United States Patent
Strongin et al.

(10) Patent No.: US 9,506,929 B2
(45) Date of Patent: Nov. 29, 2016

(54) SELECTIVE DETECTION OF AMINO GROUP CONTAINING THIOLS

(71) Applicant: OREGON STATE BOARD OF HIGHER EDUCATION ON BEHALF OF PORTLAND STATE UNIVERSITY, Portland, OR (US)

(72) Inventors: Robert M. Strongin, Portland, OR (US); Yixing Guo, Marlborough, MA (US); Lovemore Hakuna, Portland, OR (US); Mark Allen Lowry, Portland, OR (US); Jorge Omar Escobedo Córdova, Portland, OR (US)

(73) Assignee: Portland State University, Portland, OR (US)

( * ) Notice: Subject to any disclaimer, the term of this patent is extended or adjusted under 35 U.S.C. 154(b) by 58 days.

(21) Appl. No.: 14/380,704
(22) PCT Filed: Feb. 22, 2013
(86) PCT No.: PCT/US2013/027482
§ 371 (c)(1),
(2) Date: Aug. 22, 2014
(87) PCT Pub. No.: WO2013/126816
PCT Pub. Date: Aug. 29, 2013

(65) Prior Publication Data
US 2015/0010938 A1    Jan. 8, 2015

Related U.S. Application Data
(60) Provisional application No. 61/602,581, filed on Feb. 23, 2012.

(51) Int. Cl.
*G01N 33/68* (2006.01)
*C07D 265/38* (2006.01)
(Continued)

(52) U.S. Cl.
CPC ......... *G01N 33/6815* (2013.01); *C07D 265/38* (2013.01); *C07D 493/10* (2013.01); *G01N 33/52* (2013.01); *G01N 33/582* (2013.01); *G01N 33/6848* (2013.01)

(58) Field of Classification Search
CPC .................................................... G01N 33/68
USPC ...... 435/29; 436/89–90, 111, 120, 166, 172; 544/102; 549/224
See application file for complete search history.

(56) References Cited

U.S. PATENT DOCUMENTS

| 5,130,433 A | 7/1992 | Albarella et al. |
| 5,227,487 A | 7/1993 | Haugland et al. |

(Continued)

FOREIGN PATENT DOCUMENTS

| JP | 44-18580 | * 8/1969 |
| WO | WO 2005/042504 A1 | 5/2005 |

(Continued)

OTHER PUBLICATIONS

Kitson, T. M., Bioorganic Chemistry 1998, 26, 63-73.*
(Continued)

*Primary Examiner* — Arlen Soderquist
(74) *Attorney, Agent, or Firm* — Klarquist Sparkman, LLP

(57) ABSTRACT

Probes for selectively detecting compounds comprising a thiol group and an amino group ("thiols") are disclosed. Exemplary thiols include cysteine, homocysteine, and glutathione. Embodiments of the disclosed probes produce a detectable change in absorbance spectrum and/or emission spectrum when reacted with one or more thiols in solution. Methods and kits for performing the detection also are disclosed. The probes have a general formula

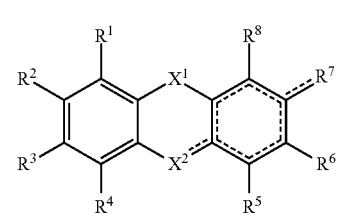

(I)

where each bond depicted as "-----" is a single or double bond; $R^1$, $R^3$-$R^6$ and $R^8$ independently are hydrogen, hydroxyl, thiol, lower alkyl, carboxyalkyl, amino, alkoxy, or halogen; $R^2$ is an α,β-unsaturated aliphatic ester; $R^7$ is oxygen, sulfur, hydrogen, hydroxyl, thiol, lower alkyl, carboxyalkyl, amino, alkoxy, or halogen, or $R^7$ and $R^8$ together form a cycloalkyl or aryl ring; $X^1$ is $CH_2$, S, NH, O, Se, $Si(CH_3)_2$, $Ge(CH_3)_2$, $Sn(CH_3)_2$, or $C(CH_3)_2$; and $X^2$ is CH, $CH_2$, N, NH, or $CR^9$ where $R^9$ is aryl.

20 Claims, 18 Drawing Sheets

(51) Int. Cl.
C07D 493/10 (2006.01)
G01N 33/52 (2006.01)
G01N 33/58 (2006.01)

(56) References Cited

U.S. PATENT DOCUMENTS

| | | | |
|---|---|---|---|
| 5,750,409 | A | 5/1998 | Herrmann et al. |
| 6,534,316 | B2 | 3/2003 | Strongin et al. |
| 2007/0220621 | A1 | 9/2007 | Clarke et al. |
| 2008/0261315 | A1 | 10/2008 | Strongin et al. |
| 2009/0104711 | A1* | 4/2009 | Sim .................. C09K 11/06 436/172 |
| 2009/0253143 | A1 | 10/2009 | Yang et al. |
| 2010/0051826 | A1 | 3/2010 | Strongin et al. |
| 2010/0275280 | A1 | 10/2010 | Clevers et al. |
| 2012/0276649 | A1 | 11/2012 | Strongin et al. |
| 2014/0120628 | A1 | 5/2014 | Strongin et al. |
| 2014/0127820 | A1 | 5/2014 | Strongin et al. |

FOREIGN PATENT DOCUMENTS

| WO | WO 2005/110109 | 11/2005 |
|---|---|---|
| WO | WO 2008/011508 | 1/2008 |
| WO | WO 2011/082354 A2 | 7/2011 |

OTHER PUBLICATIONS

Richard, J.-A. et al, Bioconjugate Chemistry 2008, 19, 1707-1718.*
Blondeau et al., "Synthesis of Some Stable 7-Halo-1, 4-thiazepines. Potential Substituted Penam Precursors," *Canadian Journal of Chemistry*, vol. 49, pp. 3866-3876 (1971).
Chang et al., "A tautomeric zinc sensor for ratiometric fluorescence imaging: Application to nitric oxide-induced release of intracellular zinc," *PNAS* 101(5):1129-1134 (2004).
Guo et al., "A Fast Response Highly Selective Probe for the Detection of Glutathione in Human Blood Plasma," *Sensors*, pp. 5940-5950 (May 8, 2012).
Huang et al., "Selenium-Mediated Micellar Catalyst: An Efficient Enzyme Model for Glutathione Peroxidase-like Catalysis," *Langmuir*, 2007, vol. 23, pp. 1518-1522 (2007).
Khatik et al., "Catalyst-Free Conjugated Addition of Thiols to α,β-Unsaturated Carbonyl Compounds in Water," *Organic Letters*, vol. 8, No. 11, pp. 2433-2436.
Leonard et al., "The Synthesis and Stereochemistry of Substituted 1, 4-Thiazepines Related to the Penicillins," *Journal of Organic Chemistry*, vol. 31, pp. 3928-3935 (1966).
Nolan et al., "Turn-On and Ratiometric Mercury Sensing in Water with a Red-Emitting Probe," *J. Am. Chem. Soc.*, 129(18):5910-5918 (Apr. 2007).
Sayyah et al., "Kinetic Studies on the Dilatometric-Free Radical Copolymerization of New Modified Laser Dye Monomer with Methyl Methacrylate and Characterization of the Obtained Copolymer," *Journal of Applied Polymer Science*, vol. 112, No. 4, pp. 2462-2471 (2009).
Shou, H. & Neckers, D.C., "Formation of Multicolor Plyometric Objects by Laser-Initiated Photopolymerization," *Journal of Imaging Science and Technology*, vol. 39, No. 1, pp. 18-26 (1995).
Wang et al., "A Colorimetric and Fluorescent Chemodosimeter for Discriminative and Simultaneous Quantification of Cysteine and Homocysteine," *Dyes and Pigments*, vol. 95, pp. 275-279 (2012).
Wei et al., "Enhanced Cyclization Rates of Large Rings Induces by a Micellar Environment," *Langmuir*, vol. 7, pp. 1336-1339 (1991).
Whitaker et al., "Spectral and photophysical studies of benzo[c]xanthene dyes: Dual emission pH sensors," *Anal. Biochem.* 194:330-344 (1991).
Yang et al., "A Seminaphthofluorescein-Based Fluorescent Chemodosimeter for the Highly Selective Detection of Cysteine," *Organic and Biomolecular Chemistry*, vol. 10, pp. 2739-2741 (2012).
Yang et al., "Conjugate Addition/Cyclization Sequence Enables Selective and Simultaneous Fluorescence Detection of Cysteine and Homocysteine," *Angewandte Chemie*, International Edition, vol. 50, pp. 10690-10693 (2011).
Yang et al., "A Convenient Preparation of Xanthene Dyes," *Journal of Organic Chemistry* 70(17):6907-6912 (Jul. 2005).
Yang et al., "An Organic White Light-Emitting Fluorophore," *Journal of the American Chemical Society* 128(43):14081-14092 (Oct. 2006).
Yang et al., "An Organic White Light-Emitting Fluorophore," *Journal of the American Chemical Society* 129:1008 (Jan. 2007).
Yang et al., "Seminaphthofluorones are a family of water-soluble, low molecular weight, NIR-emitting fluorophores," *PNAS* 105(26):8829-8834 (Jul. 2008).
Extended European Search Report, dated Sep. 4, 2015, issued in related European Patent Application No. 13752087.0.
Hakuna, et al., "A Simple Assay for Glutathione in Whole Blood," *The Analyst* 2015, 140(10):3339-3342.
Wang, et al., "Detection of Homocysteine and Cysteine," *Journal of the American Chemical Society*, American Chemical Society 2005, 127(45):15949-15958.
Examination Report, dated Apr. 20, 2016, issued for corresponding European Patent Application No. 13752087.0, 7 pages.

* cited by examiner

SELECTIVE DETECTION OF AMINO GROUP CONTAINING THIOLS

CROSS REFERENCE TO RELATED APPLICATIONS

This is the U.S. National Stage of International Application No. PCT/US2013/027482, filed Feb. 22, 2013, which was published in English under PCT Article 21(2), which in turn claims priority to U.S. Provisional Application No. 61/602,581, filed Feb. 23, 2012, each of which is incorporated herein by reference in its entirety.

ACKNOWLEDGMENT OF GOVERNMENT SUPPORT

This invention was made with government support under R01EB002044-11 awarded by the National Institutes of Health. The government has certain rights in the invention.

FIELD

Embodiments of probes, methods, and kits for selectively detecting compounds comprising a thiol group and an amino group are disclosed.

BACKGROUND

Biological thiols perform significant functions. For example, glutathione (GSH) serves as an antioxidant. It protects cells from oxidative stress by trapping free radicals that damage DNA and RNA. It also has important roles in maintaining the reducing environment in cells, catalysis, metabolism, transport, and gene regulation. GSH is the most abundant of the low molecular weight cellular thiols. It is present in millimolar concentrations; however, extracellular concentrations are relatively low, e.g., 2-20 µM in plasma. GSH is related to several diseases thought to be mediated by oxidative stress, including Alzheimer's disease, acquired immune deficiency syndrome, psoriasis, cancer, cardiovascular disease, heart attack, liver damage, leukocyte loss, Parkinson's disease, and stroke. Cysteine (Cys) is involved in protein synthesis, detoxification, and metabolic processes. Abnormal levels of Cys are related to many disorders, such as impaired growth, Alzheimer's disease, and cardiovascular disease. Cys deficiency is involved in slowed growth, hair depigmentation, edema, lethargy, liver damage, muscle and fat loss, skin lesions, and weakness (Shahrokhian, *Anal. Chem.* 2001, 73:5972-5978).

SUMMARY

Embodiments of probes for selectively detecting compounds comprising a thiol group and an amino group (referred to herein as "thiols") are disclosed. Exemplary compounds include biological thiols, such as cysteine, homocysteine, and glutathione. Embodiments of the disclosed probes when reacted with one or more thiols in solution produce a detectable change in the solution's absorbance spectrum and/or emission spectrum. Methods and kits for performing the detection also are disclosed.

Embodiments of the disclosed probes have a chemical structure according to general formula I.

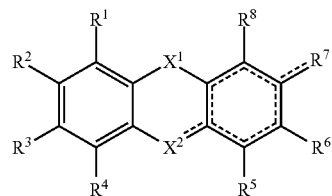

where each bond depicted as " ----- " is a single or double bond as needed to satisfy valence requirements; $R^1$, $R^3$-$R^6$ and $R^8$ independently are hydrogen, hydroxyl, thiol, lower alkyl, carboxyalkyl, amino, alkoxy, or halogen; $R^2$ is an α,β-unsaturated aliphatic ester; $R^7$ is oxygen, sulfur, hydrogen, hydroxyl, thiol, lower alkyl, carboxyalkyl, amino, alkoxy, or halogen, or $R^7$ and $R^8$ together form a cycloalkyl or aryl ring; $X^1$ is $CH_2$, S, NH, O, Se, $Si(CH_3)_2$, $Ge(CH_3)_2$, $Sn(CH_3)_2$, or $C(CH_3)_2$; and $X^2$ is CH, $CH_2$, N, NH, or $CR^9$ where $R^9$ is aryl.

In some embodiments, the probe has a structure according to general formula IA where $R^7$ is O or S, and $X^2$ is CH, $CH_2$, N, or NH.

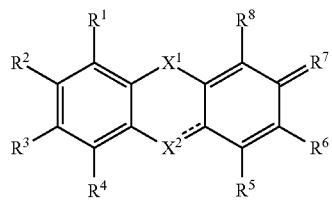

One exemplary probe according to general formula IA ("probe 8") has the chemical structure

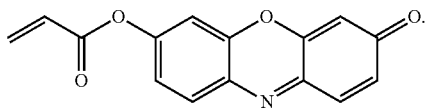

In some embodiments, $R^7$ and $R^8$ together form an aryl ring, $X^2$ is $CR^9$, and the probe has a chemical structure according to general formula II.

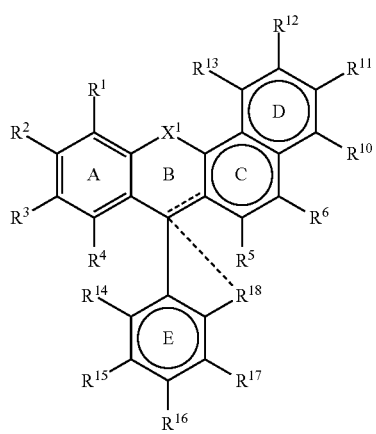

where " ----- " indicates a single or double bond as needed to satisfy valence requirements and "------" indicates an optional single bond; $R^2$ and $R^{11}$ independently are an α,β-unsaturated aliphatic ester; $R^{10}$, $R^{12}$, and $R^{13}$ independently are hydrogen, hydroxyl, thiol, lower alkyl, carboxyalkyl, amino, alkoxy, or halogen; $R^{14}$-$R^{17}$ independently are hydrogen, alkyl, acyl, carboxyl, nitro, amino, alkyl amino, or —SO$_3$H; and $R^{18}$ is hydrogen, hydroxyl, lower alkyl, lower alkoxy, —SO$_3$H or —COOR$^{19}$ where $R^{19}$ is hydrogen or lower alkyl and the bond depicted as " ----- " in ring B is a double bond, or $R^{18}$ is one or more atoms forming a ring system with rings B and E and the bond depicted as " ----- " in ring B is a single bond.

One exemplary probe according to general formula II ("probe 5") has the chemical structure:

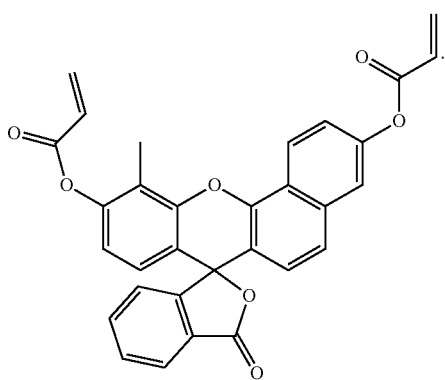

Embodiments of a method for selectively detecting a compound comprising a thiol group and an amino group include (i) preparing a reaction mixture by combining a sample potentially comprising at least one compound comprising a thiol group and an amino group with a solution comprising a probe as disclosed herein; (ii) allowing a reaction between the sample and the probe to proceed for an effective period of time to produce a detectable change in the reaction mixture's absorbance spectrum, emission spectrum, or both, where the change indicates that the compound is present; and (iii) detecting the change. In some examples, the sample comprises blood, a blood product or component, urine, or a urine product or component. In some embodiments, the reaction mixture further includes a surfactant, and the surfactant may affect probe selectivity.

Embodiments of a kit for detecting a compound comprising a thiol group and an amino group include at least one probe as disclosed herein. The kit may further comprise at least one buffer solution with a pH of 6-7.5 and, optionally, a surfactant. In some embodiments, the kit includes a plurality of disposable containers in which a reaction between the probe and the compound can be performed. An amount of the probe effective to undergo a detectable change in the absorbance spectrum, the emission spectrum, or both when reacted with a compound comprising a thiol group and an amino group may be premeasured into the plurality of disposable containers. The kit also may include a color comparison chart for evaluating a color change produced by the reaction.

The foregoing and other objects, features, and advantages of the invention will become more apparent from the following detailed description, which proceeds with reference to the accompanying figures.

Figure 17:
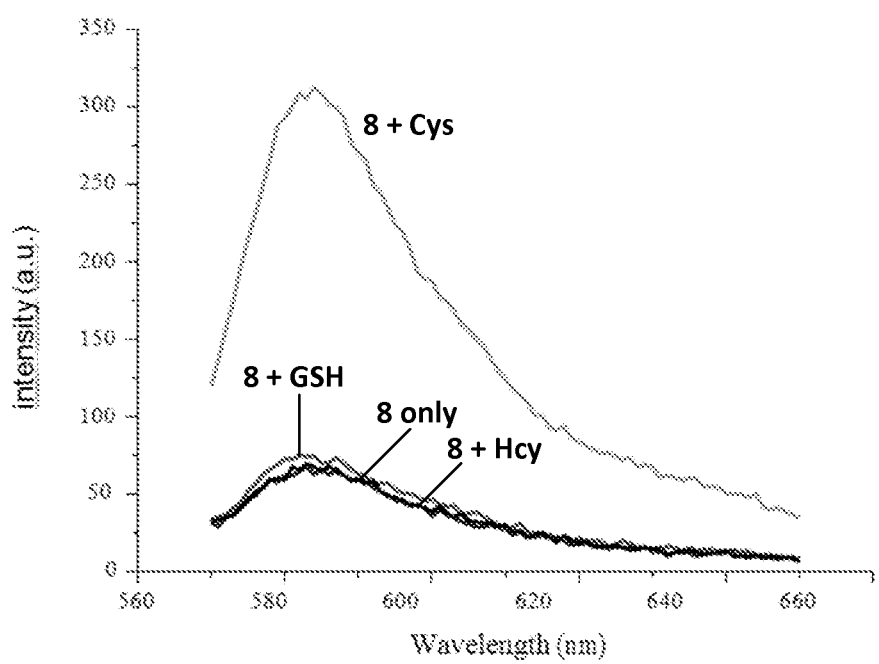

FIG. 17 shows fluorescence spectra ($\lambda_{ex}$=565 nm) obtained when probe 8 (2.5 µM) was combined with 2 equivalents of Cys, Hcy, or GSH is phosphate-buffered media (50 mM, pH=7.4) with 0.3 mM Triton X-100.

Figure 18:
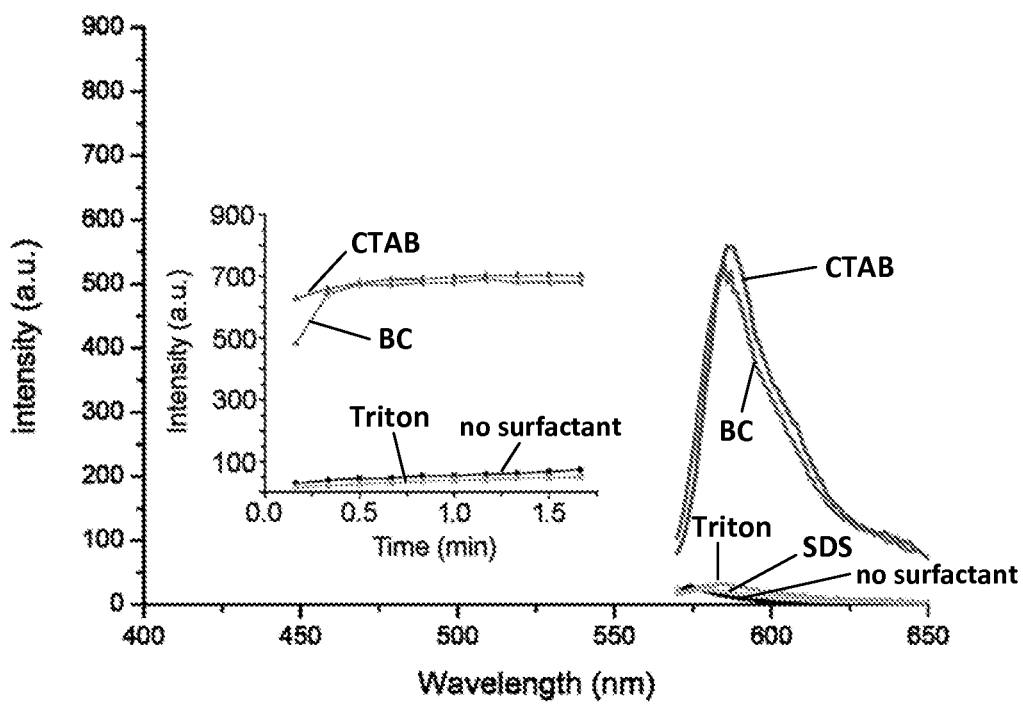

FIG. 18 shows fluorescence spectra obtained when probe 8 (2.5 µM) was combined with 2 equivalents of GSH in phosphate-buffered media (50 mM, pH=7.4) with 10 mM SDS, 0.3 mM Triton X-100, 0.05 mM BC, or 2 mM CTAB. Spectra were obtained immediately upon addition of the surfactants; the inset shows time-dependent fluorescence changes ($\lambda_{em}$=587 nm) of the same system.

Figure 19:
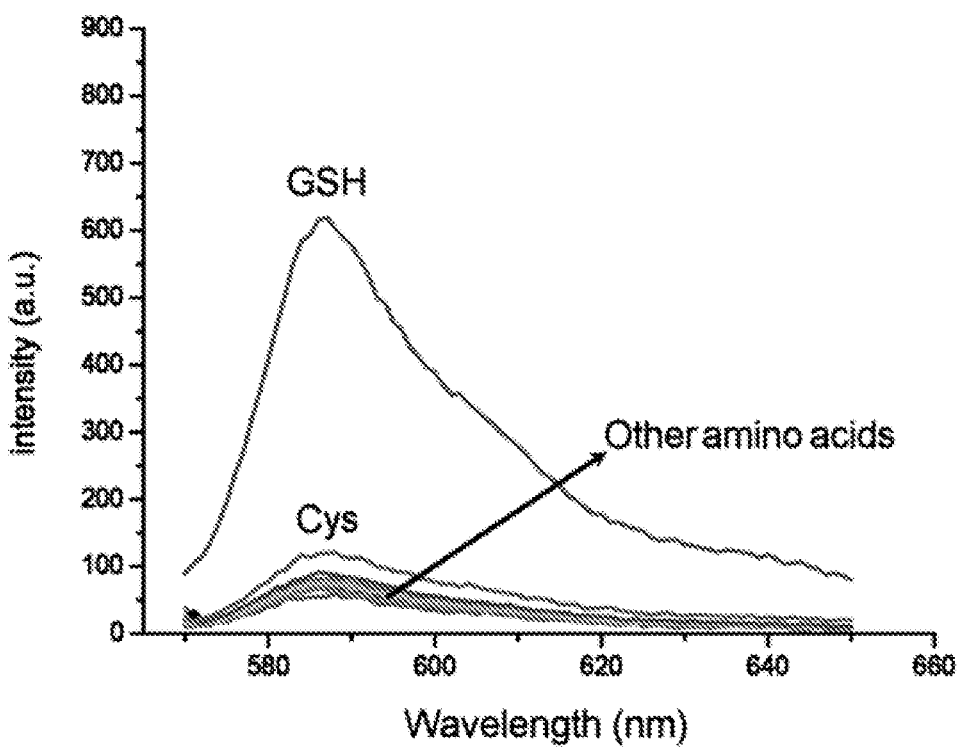

FIG. 19 shows fluorescence spectra obtained from the reaction of probe 8 with Cys, Hcy, GSH, and other amino acids in buffered 2.0 mM CTAB; selective detection of GSH resulted.

Figure 20:
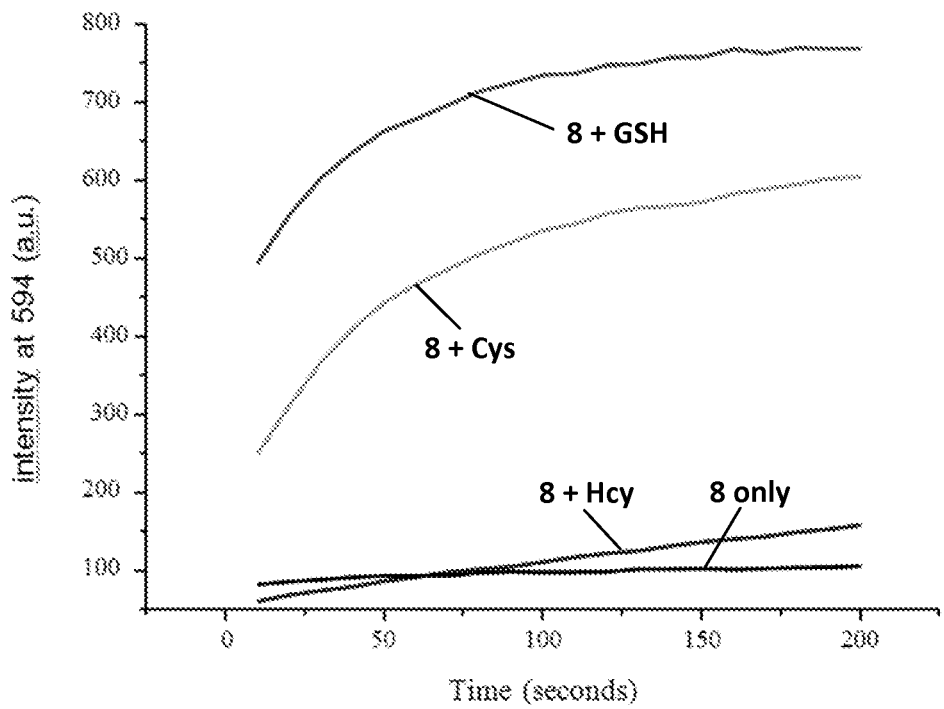

FIG. 20 shows time-dependent changes in fluorescence emission ($\lambda_{ex}/\lambda_{em}$=565/594 nm) when probe 8 was combined with Cys, Hcy, or GSH in DMSO/H$_2$O 1:1 buffered at pH 7.4.

Figure 21:
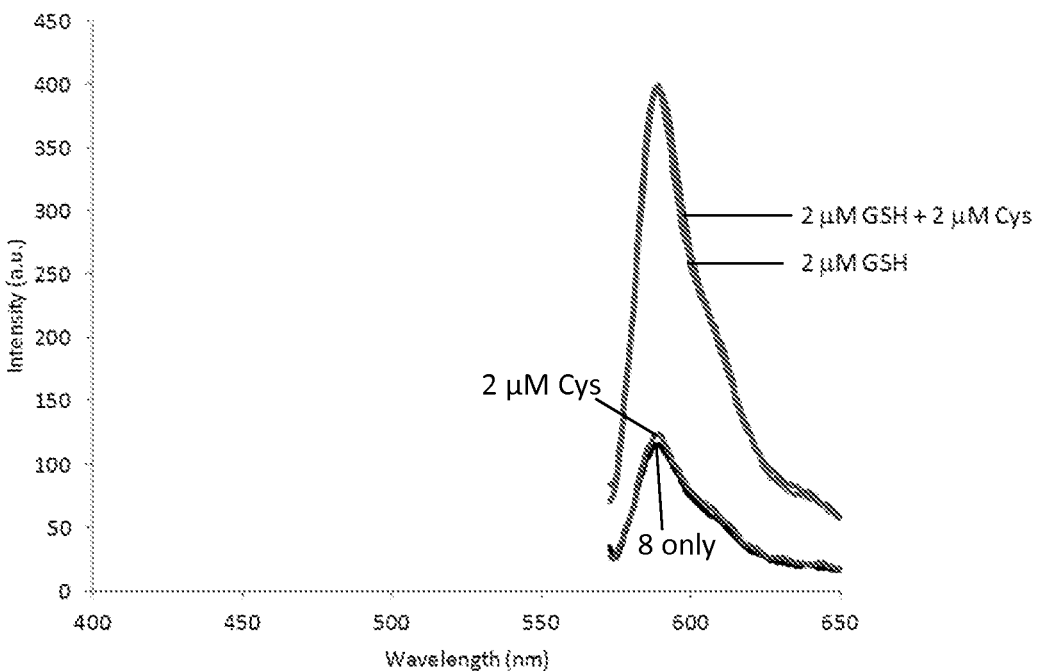

FIG. 21 shows fluorescence spectra of the CTAB-mediated response of probe 8 towards 2 µM Cys, 2 µM GSH, or a combination of 2 µM Cys and 2 µM GSH.

Figure 22:
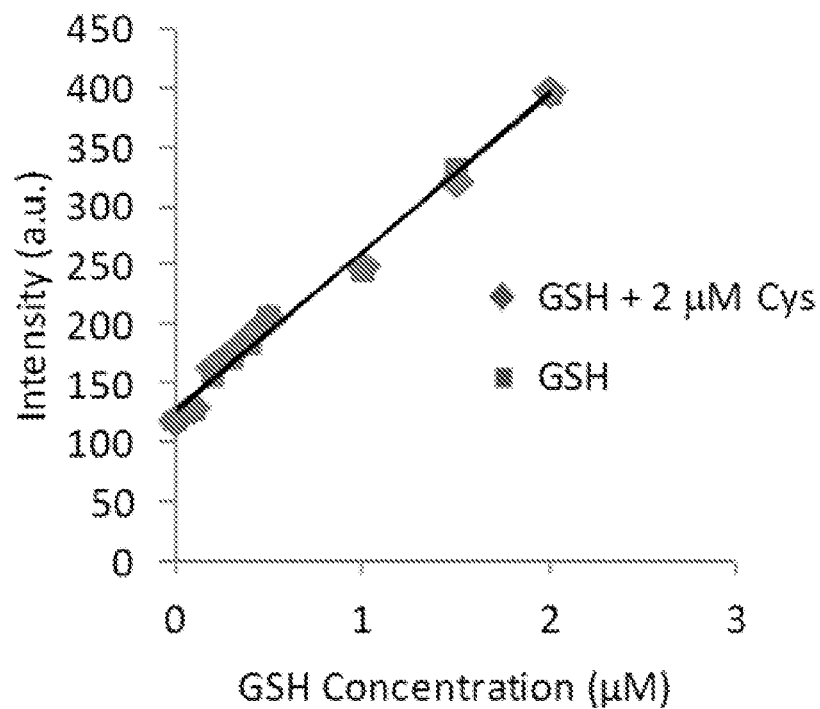

FIG. 22 is a graph illustrating the relationship between fluorescence intensity and GSH concentration when GSH is reacted with probe 8 at pH 7.4 (phosphate buffer, 50 mM), or with probe 8 and 2 µM Cys; reaction time of 2 minutes.

Figure 23:
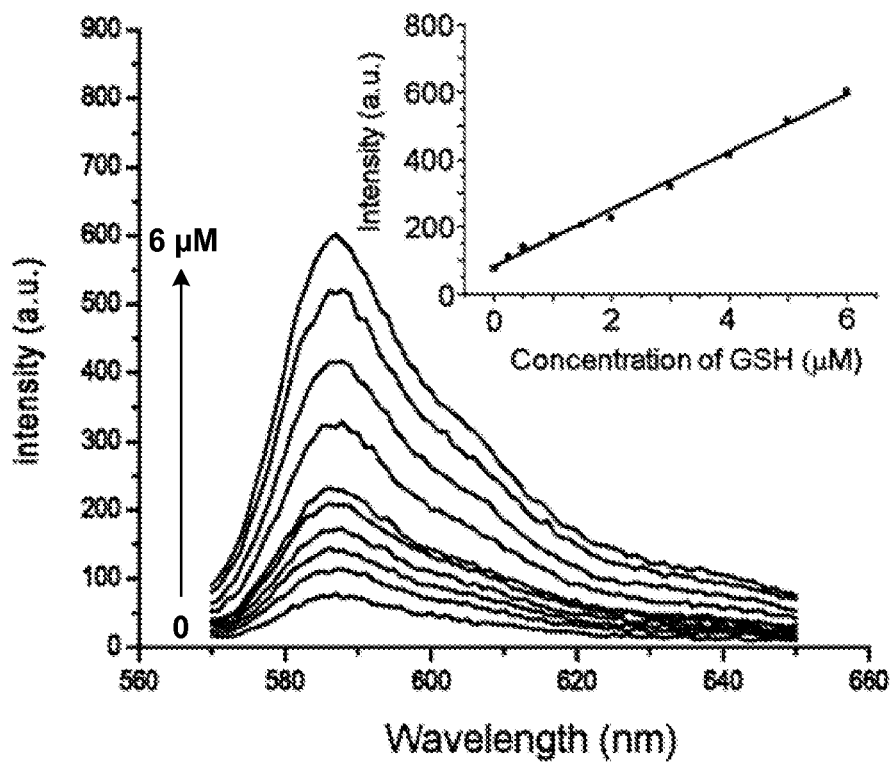

FIG. 23 shows fluorescence spectra obtained from the reaction of probe 8 with varying concentrations of GSH in buffered 2.0 mM CTAB; inset is a graph illustrating the linear relationship between fluorescence intensity and GSH concentration when GSH is reacted with probe 8 in buffered 2.0 mM CTAB.

Figure 24:
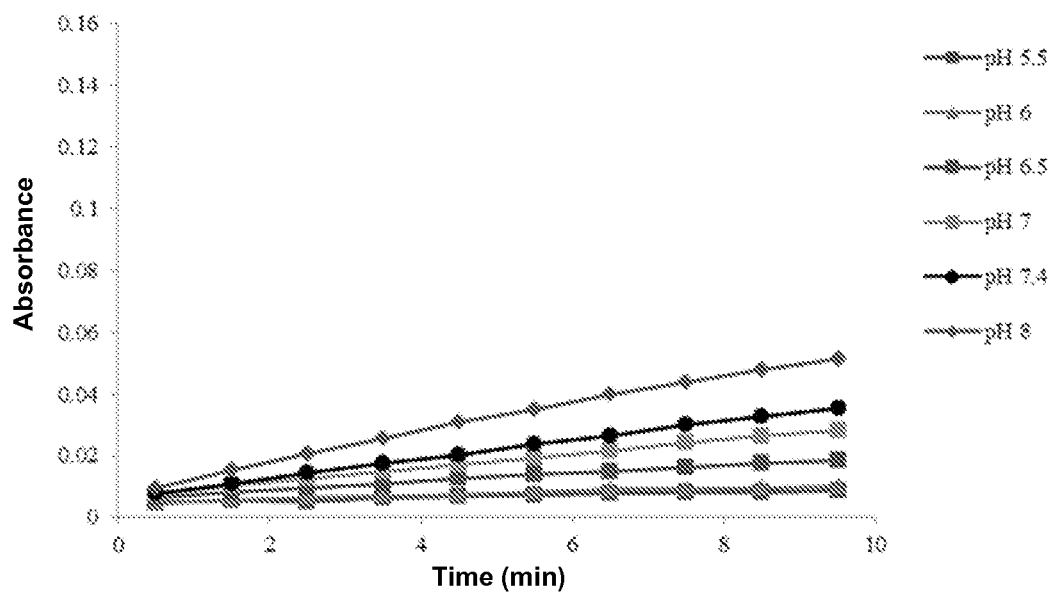

FIG. 24 is a graph illustrating the time-dependent absorbance changes (at 580 nm) of probe 8 in CTAB media buffered at pH 5.5 to 8.

Figure 25:
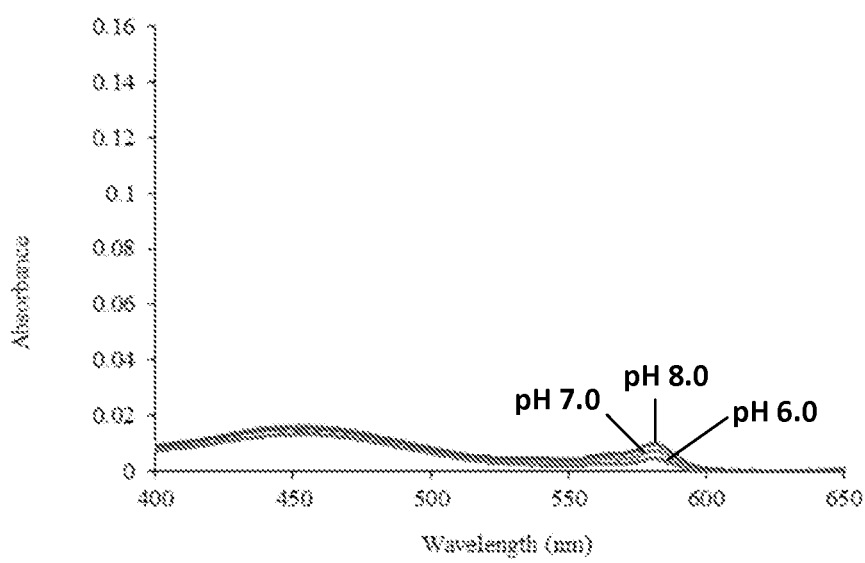

FIG. 25 shows absorbance spectra of probe 8 in CTAB media buffered at pH 6.0, 7.0, and 8.0 after one minute.

Figure 26:
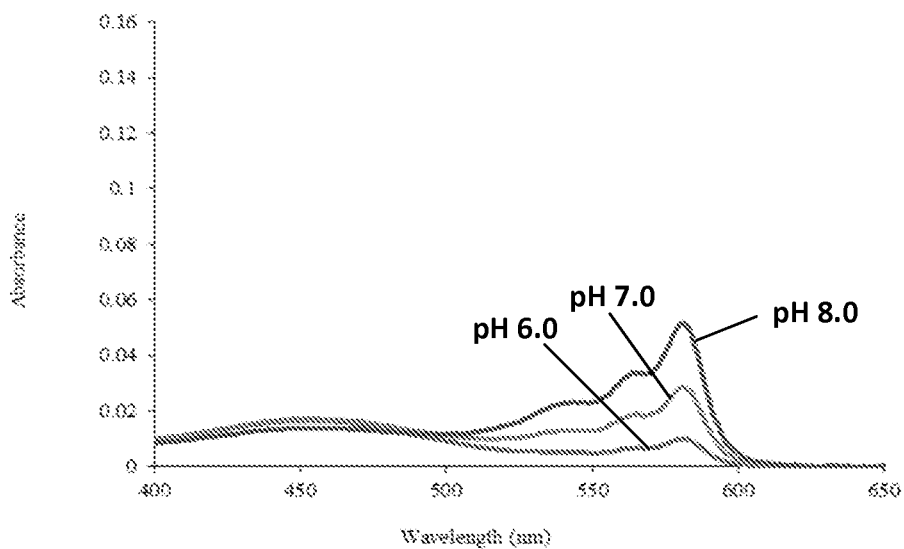

FIG. 26 shows absorbance spectra of probe 8 in CTAB media buffered at pH 6.0, 7.0, and 8.0 after 10 minutes.

Figure 27:
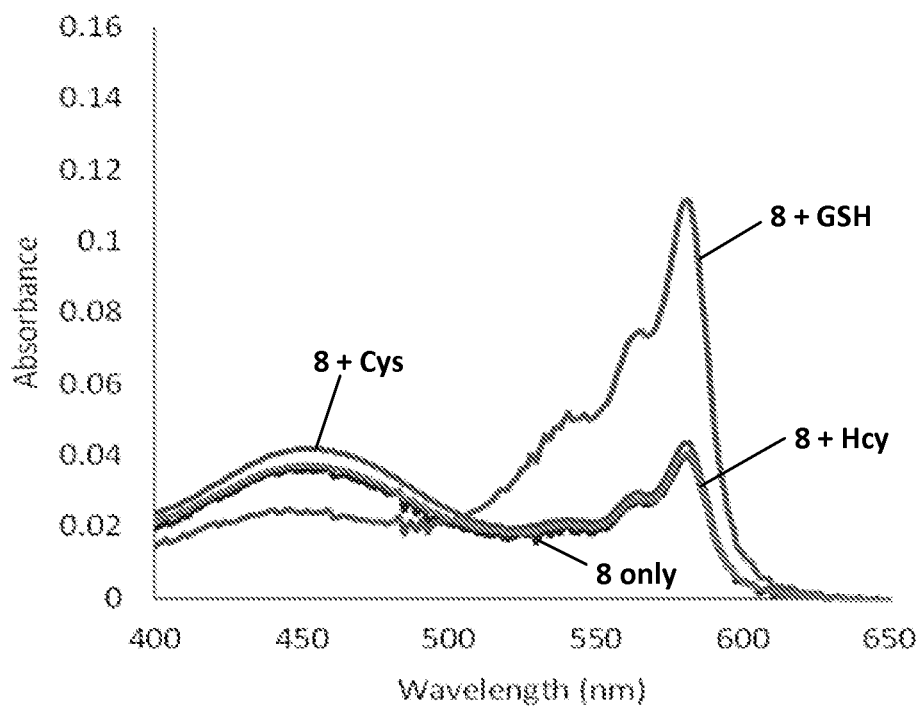

FIG. 27 shows absorbance spectra of probe 8 with Cys, Hcy, and GSH in CTAB media buffered at pH 6.0 after 20 minutes.

Figure 28:
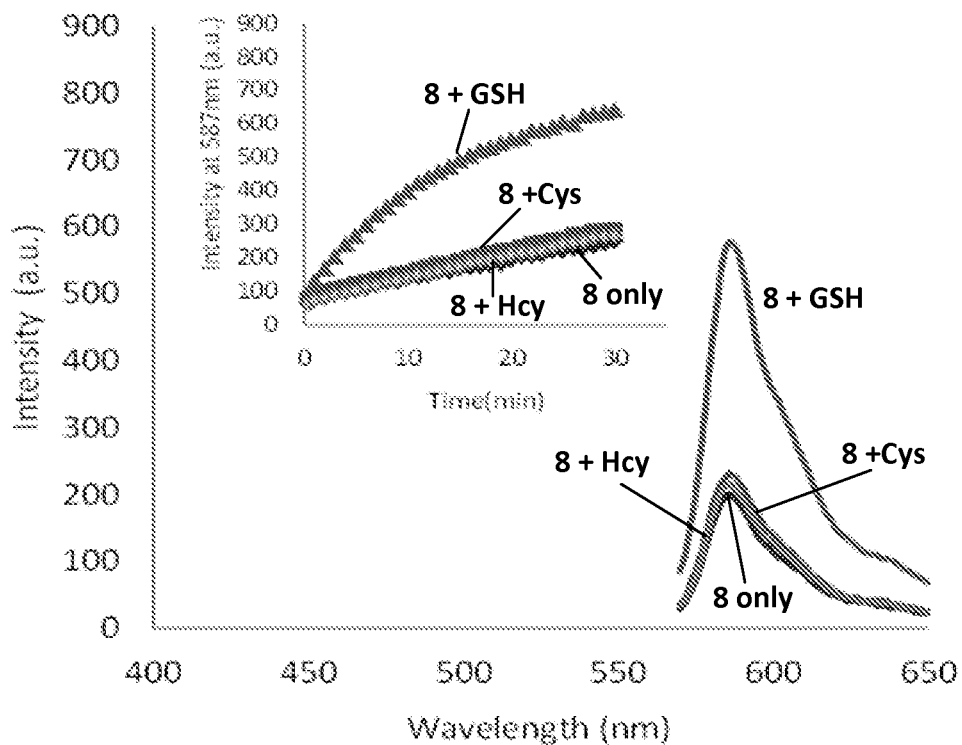

FIG. 28 shows fluorescence spectra ($\lambda_{ex}$=565 nm) of probe 8 with Cys, Hcy, and GSH in CTAB media buffered at pH 6.0 after 20 minutes; the inset shows the time-dependent fluorescence changes ($\lambda_{em}$=587 nm).

Figure 29:
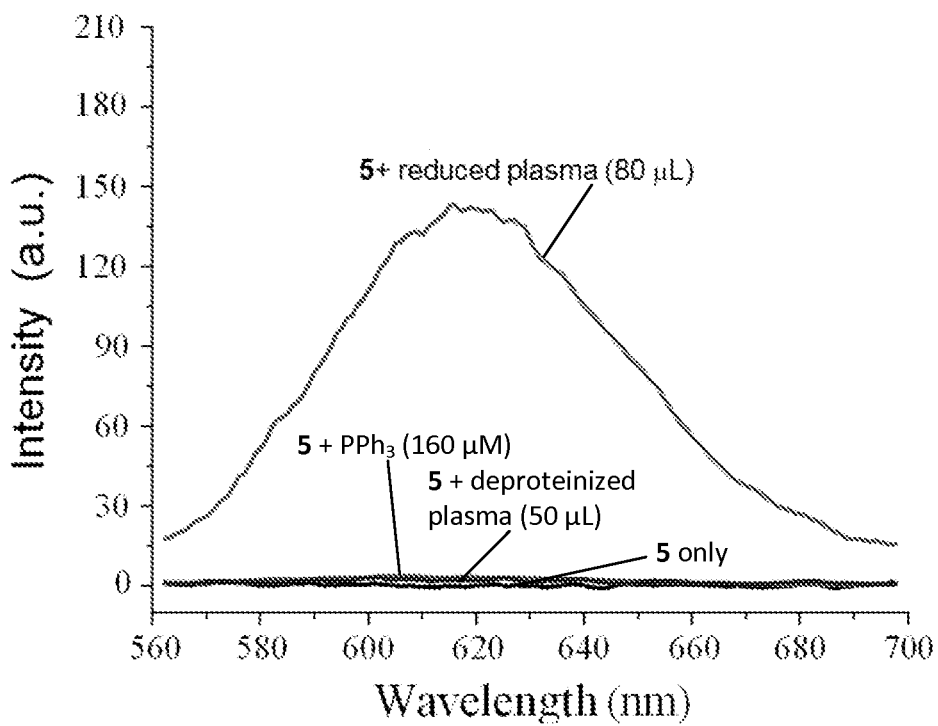

FIG. 29 shows fluorescence spectra ($\lambda_{ex}$=550 nm) of probe 5 with triphenylphosphine, deproteinized human plasma, and reduced deproteinized plasma in pH 7.4 HEPES buffer solution (0.1 M) in the presence of 1.0 mM CTAB; spectra were obtained after 25 minutes.

Figure 30:
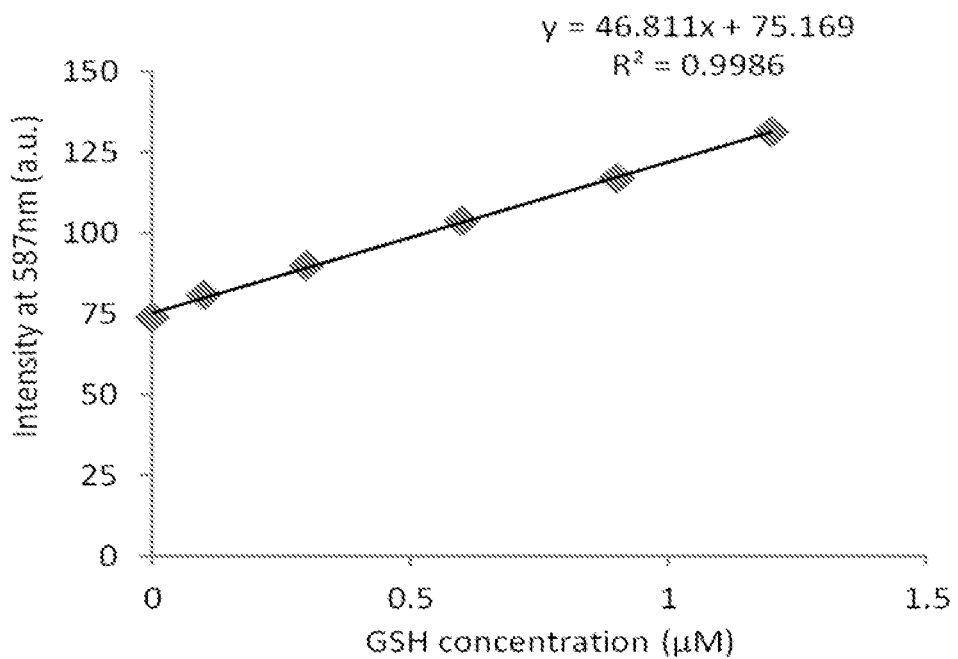

FIG. 30 is a calibration curve of probe 8 (1.0 µM) in 2.0 mM CTAB media buffered at pH 6 (phosphate buffer, 50 mM) showing a linear relationship between fluorescence intensity ($\lambda_{ex}$=565 nm, $\lambda_{em}$=587 nm) and GSH concentration (0.1-1.2 µM). Measurements were taken 8 minutes after mixing.

Figure 31:
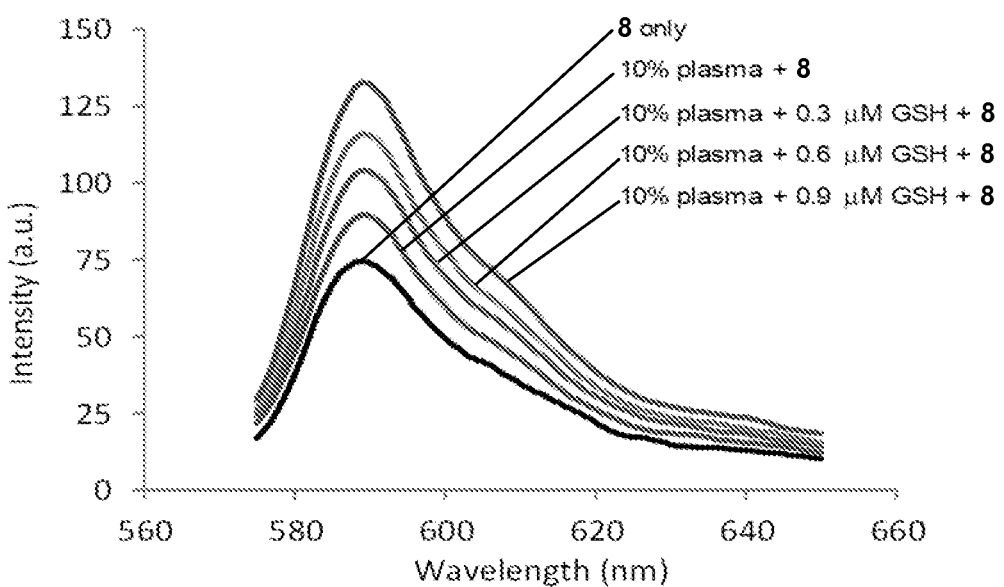

FIG. 31 shows fluorescence spectra ($\lambda_{ex}$=565 nm) of probe 8 (1.0 µM) upon addition of GSH (0-1.0 µM) to 10% deproteinized plasma diluted with 2.0 mM CTAB media buffered at pH 6.0 (phosphate buffer, 50 mM). Measurements were taken 8 minutes after mixing.

Figure 32:
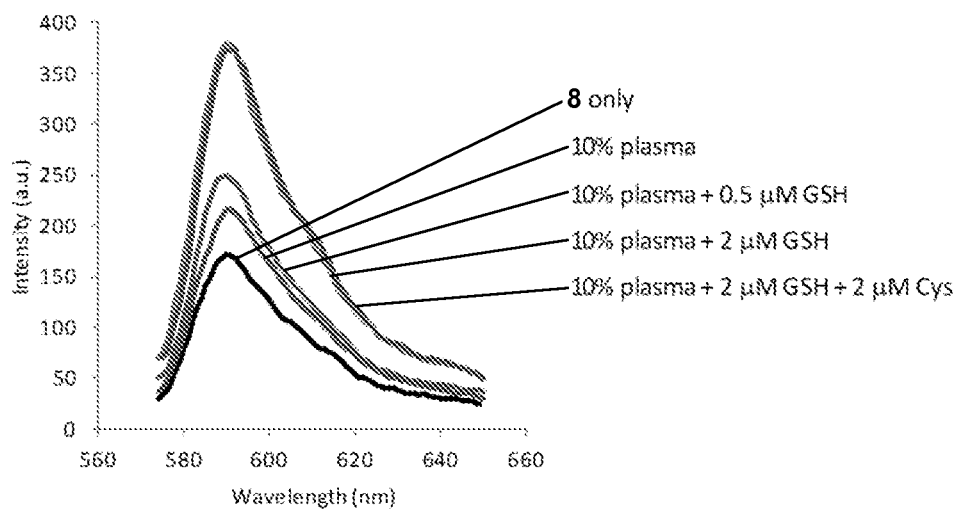

FIG. 32 shows fluorescence spectra ($\lambda$ex=565 nm) obtained when probe 8 (1.5 µM) was reacted with GSH (0-2.0 µM) or a mixture of GSH (2 µM) and Cys (2 µM) in 10% deproteinized plasma diluted with 2.0 mM CTAB media buffered at pH 6.0 (phosphate buffer, 50 mM).

Figure 33:
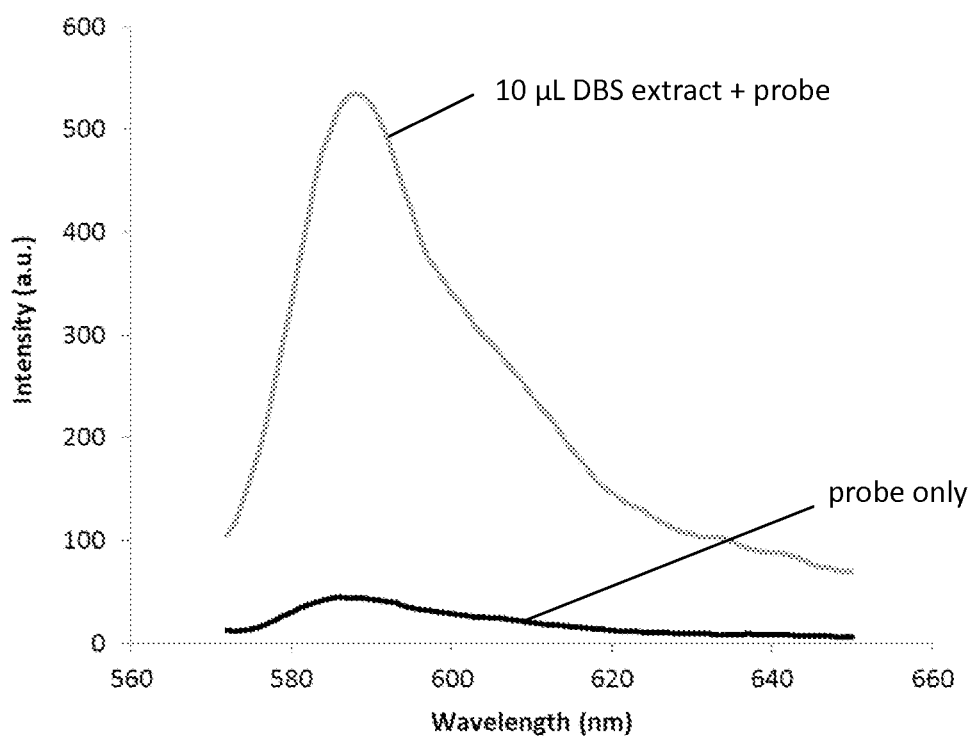

FIG. 33 is a fluorescence spectrum ($\lambda$ex=565 nm) obtained when probe 8 was combined with a dried blood spot (DBS) extract in 2.0 mM CTAB media buffered at pH 6.0 (phosphate buffer, 50 mM); the probe reacted with GSH in the extract.

DETAILED DESCRIPTION

Disclosed herein are embodiments of probes that can selectively detect and differentiate between GSH and Cys at physiologic pH. Embodiments of disclosed probes also can discriminate GSH and Cys from other amino acids and thiols (e.g., Hcy) at physiologic pH. Embodiments of the disclosed probes include a fluorophore moiety to facilitate detection and a moiety capable of undergoing a condensation-cyclization reaction (referred to as a "cyclization moiety") with GSH and/or Cys. In some embodiments, the cyclization moiety is an α,β-unsaturated carbonyl moiety, which is covalently bonded to the fluorophore moiety.

I. TERMS AND DEFINITIONS

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Definitions of other common terms in chemistry may be found in Richard J. Lewis, Sr. (ed.), *Hawley's Condensed Chemical Dictionary*, published by John Wiley & Sons, Inc., 1997 (ISBN 0-471-29205-2).

In order to facilitate review of the various embodiments of the disclosure, the following explanations of specific terms are provided:

Absorbance: The retention by a compound or substance of certain wavelengths of radiation incident upon it; a measure of the amount of light at a particular wavelength absorbed as the light passes through a compound or substance, or through a solution of a compound or substance.

Acrylate ester: A group having a general formula —OC(O)CR═CR'R", where R, R' and R" individually are hydrogen, halogen, hydroxyl, lower alkoxy, lower aliphatic, or aryl.

Aliphatic: A substantially hydrocarbon-based compound, or a radical thereof (e.g., $C_6H_{13}$, for a hexane radical), including alkanes, alkenes, alkynes, including cyclic versions thereof, and further including straight- and branched-chain arrangements, and all stereo and position isomers as well. Unless expressly stated otherwise, an aliphatic group contains from one to twenty-five carbon atoms; for example, from one to fifteen, from one to ten, from one to six, or from one to four carbon atoms. The term "lower aliphatic" refers to an aliphatic group containing from one to ten carbon atoms. An aliphatic chain may be substituted or unsubstituted. An aliphatic group can be substituted with one or more substituents (up to two substituents for each methylene carbon in an aliphatic chain, or up to one substituent for each carbon of a —C═C— double bond in an aliphatic chain, or up to one substituent for a carbon of a terminal methine group). Exemplary aliphatic substituents include, for instance, amine, amide, sulfonamide, halogen, cyano, carboxyl, hydroxyl, mercapto, trifluoromethyl, alkyl, alkoxy, alkylthio, thioalkoxy, arylalkyl, heteroaryl, alkylamino, dialkylamino, or other functionality.

Alkyl: A hydrocarbon group having a saturated carbon chain. The chain may be branched or unbranched. The term lower alkyl means the chain includes 1-10 carbon atoms.

Alkoxy: A functional group having the formula —OR where R is an alkyl group. The term lower alkoxy means that the alkyl group includes 1-10 carbon atoms.

Aromatic or aryl: Compounds or groups that typically are unsaturated, cyclic hydrocarbons having alternate single and double bonds. Benzene, a 6-carbon ring containing three double bonds, is a typical aromatic compound.

BC: Benzalkonium chloride, benzyl-dimethyl-tridecyl-azanium chloride.

Carboxyalkyl: A group having a general formula —C(O)OR, where R is an alkyl group.

Carboxyl: A group having a general formula —COOH.

CTAB: Cetyltrimethylammonium bromide

Cyclization moiety: As used herein, the term "cyclization moiety" refers to a portion of a molecule capable of undergoing a condensation-cyclization reaction with a target compound, such as a compound comprising a thiol group and an amino group.

Cys: Cysteine

Detect: To determine if an agent (such as a target molecule) is present or absent, for example, in a sample. "Detecting" refers to any method of determining if something exists, or does not exist, such as determining if a target molecule is present in a biological sample. For example, "detecting" can include using a visual or a mechanical device to determine if a sample displays a specific characteristic.

Effective period of time: As defined herein, an effective period of time is a sufficient amount of time to allow a chemical reaction to occur. With respect to the present disclosure, an effective period of time is an amount of time sufficient to allow condensation of a thiol-containing compound with an embodiment of the disclosed probes and subsequent cyclization of the thiol-containing compound to occur.

Emission or emission signal: The light of a particular wavelength generated from a source. In particular examples, an emission signal is emitted from a fluorophore after the fluorophore absorbs light at its excitation wavelength(s).

Ester: A chemical compound derived from an organic acid (general formula: $RCO_2H$) where the hydrogen of the —OH (hydroxyl) group is replaced by an aliphatic, alkyl or aryl group. A general formula for an ester derived from an organic acid is shown below:

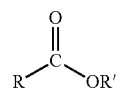

where R and R' denote virtually any group, including aliphatic, substituted aliphatic, aryl, arylalkyl, heteroaryl, etc. An ester substituent has the general formula —OC(O)R.

Fluorescence: The emission of visible radiation by an atom or molecule passing from a higher to a lower electronic state, wherein the time interval between absorption and emission of energy is $10^{-8}$ to $10^{-3}$ second. Fluorescence occurs when the atom or molecule absorbs energy from an excitation source (e.g., an ultraviolet lamp) and then emits the energy as visible radiation.

Fluorophore or fluorogen: A compound capable of fluorescence, such as a fluorescent dye. The term "fluorophore" also refers to the portion of a molecule that causes the molecule to fluoresce when exposed to an excitation source.

Functional group: A specific group of atoms within a molecule that is responsible for the characteristic chemical reactions of the molecule. Exemplary functional groups include, without limitation, alkane, alkene, alkyne, arene, halo (fluoro, chloro, bromo, iodo), epoxide, hydroxyl, carbonyl (ketone), aldehyde, carbonate ester, carboxylate, ether, ester, peroxy, hydroperoxy, carboxamide, amine (primary, secondary, tertiary), ammonium, imide, azide, cyanate, isocyanate, thiocyanate, nitrate, nitrite, nitrile, nitroalkane, nitroso, pyridyl, phosphate, sulfonyl, sulfide, thiol (sulfhydryl), disulfide.

GSH: Glutathione

Hcy: Homocysteine

HEPES: 2-[4-(2-hydroxyethyl)piperazin-1-yl]ethanesulfonic acid

Probe: As used herein, the term "probe" refers to a molecule capable of selectively reacting with a molecule of interest (i.e., a molecule for which the presence and/or concentration is to be determined) and producing a detectable signal or change as a result of the reaction. A detectable signal or change may include a change in the absorbance spectrum and/or emission spectrum of the probe and/or the molecule of interest.

SDS: Sodium dodecyl sulfate

Substituent: An atom or group of atoms that replaces another atom in a molecule as the result of a reaction. The term "substituent" typically refers to an atom or group of atoms that replaces a hydrogen atom on a parent hydrocarbon chain or ring.

Substituted: A fundamental compound, such as an aryl or aliphatic compound, or a radical thereof, having coupled thereto, typically in place of a hydrogen atom, a substituent. For example, substituted aryl compounds or substituents may have an aliphatic group coupled to the closed ring of the aryl base, such as with toluene. Again solely by way of example and without limitation, a long-chain hydrocarbon may have a substituent bonded thereto, such as one or more halogens, an aryl group, a cyclic group, a heteroaryl group or a heterocyclic group. Unless expressly referred to as "unsubstituted," functional groups recited herein (e.g., aliphatic, alkyl, alkoxy, amino, aryl, cycloalkyl, ester, etc.) can either be unsubstituted or substituted.

Surfactant: A compound that reduces surface tension when dissolved in water or aqueous solutions. Surfactants typically are amphiphilic organic compounds, i.e., organic compounds that contain both hydrophobic groups and hydrophilic groups. Surfactants may be characterized by their hydrophilic groups, or heads. A non-ionic surfactant includes no formal charge in its head. Ionic surfactants include hydrophilic groups having a net charge. If the charge is negative, the surfactant is an anionic surfactant. If the charge is positive, it is a cationic surfactant. If the head contains two oppositely charged groups, it is a zwitterionic surfactant.

Thiol: A functional group having the formula —SH. As used herein with respect to a compound, the term "thiol" refers to a compound comprising a thiol group and an amino group.

II. OVERVIEW OF REPRESENTATIVE EMBODIMENTS

Embodiments of probes for selectively detecting compounds comprising a thiol group and an amino group (referred to herein as "thiols") are disclosed. Exemplary compounds include biological thiols, such as cysteine, homocysteine, and glutathione. Embodiments of the disclosed probes when reacted with one or more thiols in solution produce a detectable change in the solution's absorbance spectrum and/or emission spectrum. Methods and kits for performing the detection also are disclosed.

Embodiments of the disclosed probes have a chemical structure according to general formula I.

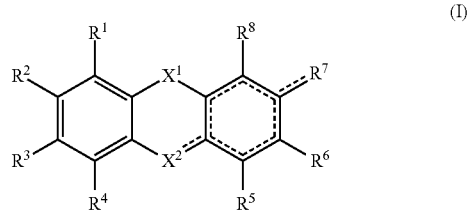

where each bond depicted as " ----- " is a single or double bond as needed to satisfy valence requirements; $R^1$, $R^3$-$R^6$ and $R^8$ independently are H, hydroxyl, thiol, lower alkyl, carboxyalkyl, amino, alkoxy, or halogen; $R^2$ is an α,β-unsaturated aliphatic ester; $R^7$ is O, S, H, hydroxyl, thiol, lower alkyl, carboxyalkyl, amino, alkoxy, or halogen, or $R^7$ and $R^8$ together form a cycloalkyl or aryl ring; $X^1$ is $CH_2$, S, NH, O, Se, $Si(CH_3)_2$, $Ge(CH_3)_2$, $Sn(CH_3)_2$, or $C(CH_3)_2$; and $X^2$ is CH, $CH_2$, N, NH, or $CR^9$ where $R^9$ is aryl.

In some embodiments, $X^1$ is O or S, and $R^7$ is O or S, or $R^7$ and $R^8$ together form an aryl ring. In any or all of the above embodiments, $R^2$ may be an acrylate ester. In any or all of the above embodiments, $R^1$ and $R^3$-$R^6$ independently may be H or lower alkyl. In some embodiments, $R^1$ is lower alkyl and $R^3$-$R^6$ are H. In some embodiments, $R^7$ is O or S and $R^8$ is H. In any or all of the above embodiments, $X^1$ may be O, $X^2$ may be N or $CR^9$, $R^1$ may be lower alkyl or H, $R^2$ may be an acrylate ester, $R^3$-$R^6$ may be H, and $R^7$ may be O and $R^8$ may be H, or $R^7$ and $R^8$ together may form an aryl ring.

In some embodiments, $R^7$ is O or S and $X^2$ is CH, $CH_2$, N or NH. In any or all of the above embodiments, $R^7$ may be O, and $X^2$ may be CH or N. In any or all of the above embodiments, $R^2$ may be an acrylate ester. In some embodiments, $R^2$ is an acrylate ester, $R^7$ is O, and $X^2$ is CH or N. In some embodiments, $R^2$ is an acrylate ester, $R^7$ is O, $X^1$ is O, and $X^2$ is CH or N. In any or all embodiments where $R^2$ is an acrylate ester, $R^7$ is O, $X^1$ is O, and $X^2$ is CH or N, $R^1$, $R^3$-$R^6$, and $R^8$ independently may be H or lower alkyl. An exemplary probe has the structure below.

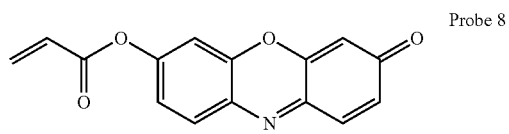 [SMILES: C=CC(=O)Oc1ccc2nc3ccc(=O)cc-3oc2c1]

In some embodiments, $R^7$ and $R^8$ together form an aryl ring and $X^2$ is $CR^9$. In such embodiments, the compound has a chemical structure according to general formula II:

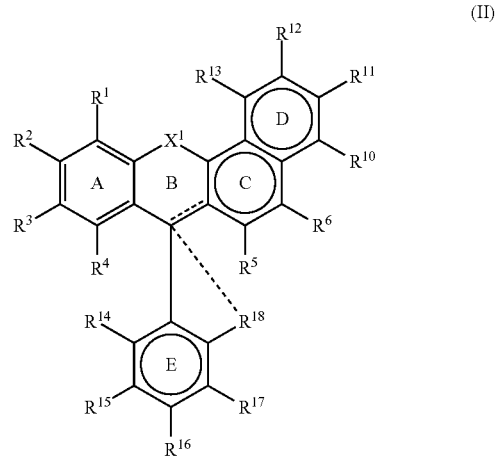

where " ----- " indicates a single or double bond as needed to satisfy valence requirements and "------" indicates an optional single bond; $R^2$ and $R^{11}$ independently are an α,β-unsaturated aliphatic ester; $R^{10}$, $R^{12}$, and $R^{13}$ independently are hydrogen, hydroxyl, thiol, lower alkyl, carboxyalkyl, amino, alkoxy, or halogen; $R^{14}$-$R^{17}$ independently are hydrogen, alkyl, acyl, carboxyl, nitro, amino, alkyl amino, or —$SO_3H$; and $R^{18}$ is hydrogen, hydroxyl, lower alkyl, lower alkoxy, —$SO_3H$ or —$COOR^{19}$ where $R^{19}$ is hydrogen or lower alkyl and the bond depicted as " ----- " in ring B is a double bond, or $R^{18}$ is one or more atoms forming a ring system with rings B and E and the bond depicted as " ----- " in ring B is a single bond.

In some embodiments, each of $R^2$ and $R^{11}$ is an acrylate ester. In any or all of the above embodiments, $R^{18}$ may be —RCOOH or $R^{18}$ may be —C(O)O— and form a ring system with rings B and E. In any or all of the above embodiments, $R^1$, $R^3$-$R^6$, $R^{10}$ and $R^{12}$-$R^{17}$ independently may be H or lower alkyl. In some embodiments, $R^1$ is lower alkyl, and $R^3$-$R^6$, $R^{10}$ and $R^{12}$-$R^{17}$ are H; optionally, $X^1$ is O. An exemplary probe according to general formula II has the structure below.

Probe 5

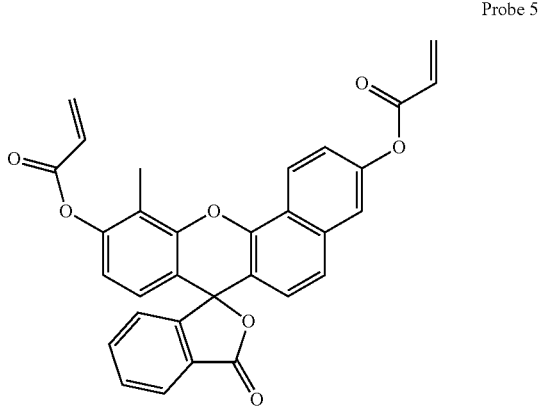 [SMILES: C=CC(=O)Oc1ccc2c3c(ccc2c1)C1(OC(=O)c2ccccc21)c1ccc(OC(=O)C=C)c(C)c1O3]

Embodiments of a method for selectively detecting a compound comprising a thiol group and an amino group include (i) combining a sample potentially comprising at least one compound comprising a thiol group and an amino group with a solution comprising a probe having a structure according to general formula I to produce a reaction mixture; (ii) allowing a reaction between the sample and the probe to proceed for an effective period of time to produce a detectable change in the reaction mixture's absorbance spectrum, emission spectrum, or both, where the change indicates that the compound is present; and (iii) detecting the change. In some embodiments, the compound is cysteine, homocysteine, glutathione, or a combination thereof.

In any or all of the above embodiments, the effective period of time may be ≤60 minutes. In any or all of the above embodiments, the sample may comprise blood, a blood product or component, urine, or a urine product or component. In one embodiment, the method further includes obtaining plasma, reducing the plasma by addition of a reducing agent, precipitating proteins in the plasma, separating precipitated proteins from the plasma to form the sample, and subsequently combining the sample with the solution comprising the probe. In another embodiment, the method further includes obtaining a dried blood spot prepared by spotting whole blood onto an absorbent material and allowing the blood to dry, extracting the dried blood spot with a solvent to produce an extract, reducing the extract by addition of a reducing agent to form a reduced extract, fractionating the reduced extract to obtain the sample, and subsequently combining the sample with the solution comprising the probe.

In any or all of the above embodiments, detecting the change may include (i) comparing a color of the reaction mixture before the reaction to a color of the reaction mixture after the reaction, (ii) detecting a change in absorbance of the reaction mixture at one or more wavelengths after the reaction has proceeded for the effective period of time, (iii) comparing an absorbance spectrum of the reaction mixture at a first time after combining the sample and the probe to an absorbance spectrum of the reaction mixture after the reaction has proceeded for the effective period of time, (iv) detecting a change in emission of the reaction mixture at one or more wavelengths after the reaction has proceeded for the effective period of time, (v) comparing an emission spectrum of the reaction mixture at a first time after combining the sample and the probe to an emission spectrum of the solution after the reaction has proceeded for the effective period of time, (vi) or any combination thereof.

In any or all of the above embodiments, the probe may be probe 8. In some embodiments, detecting the compound comprises detecting fluorescence of the reaction mixture at 580-590 nm. In some embodiments, when the probe is probe 8 and the compound is glutathione, the reaction mixture further includes a cationic surfactant. Exemplary cationic surfactants include cetyltrimethylammonium bromide and benzalkonium chloride. In some embodiments, when the probe is probe 8 and the compound is cysteine, the reaction mixture further includes a surfactant other than a cationic surfactant, e.g., sodium dodecyl sulfate or polyethylene glycol tert-octylphenyl ether. In certain embodiments, the reaction mixture further comprises dimethyl sulfoxide.

In any or all of the above embodiments, the compound may be cysteine and the probe may be probe 5. In some embodiments, the reaction mixture further comprises cetyltrimethylammonium bromide.

Embodiments of a kit for detecting at least one compound comprising a thiol group and an amino group include an embodiment of the disclosed probes having a structure according to general formula I. In some embodiments, the kit further includes at least one buffer solution with a pH of 6-7.5. The buffer solution may include a surfactant. In some embodiments, the surfactant is cetyltrimethylammonium bromide, benzalkonium chloride, sodium dodecyl sulfate, or polyethylene glycol tert-octylphenyl ether.

In any or all of the above embodiments, the kit may further include a plurality of disposable containers in which a reaction between the probe and the compound can be performed. In some embodiments, an amount of the probe effective to undergo a detectable change in the absorbance spectrum, the emission spectrum, or both when reacted with a compound comprising a thiol group and an amino group is premeasured into the plurality of disposable containers.

In any or all of the above embodiments, the kit may include a color comparison chart for evaluating a color change produced by a reaction between (a) the probe and (b) cysteine, homocysteine, glutathione, or a combination thereof. In any or all of the above embodiments, the probe may be probe 5 or probe 8.

III. OVERVIEW OF CONJUGATE ADDITION-CYCLIZATION

Cysteine is capable of undergoing condensation with certain acrylates to form substituted 1,4-thiazepines (Blondeau et al., *Can. J. Chem.* 1971, 49, 3866-3876; Leonard et al., *J. Org. Chem.* 1966, 31, 3928-3935). The reaction involves the conjugate addition of Cys to acrylates (1; R is alkyl, such as methyl) to generate thioether (2a), which can further undergo an intramolecular cyclization to yield the desired compound 3a (3-carboxy-5-oxoperhydro-1,4-thiazepine), as illustrated in Scheme 1.

Scheme 1

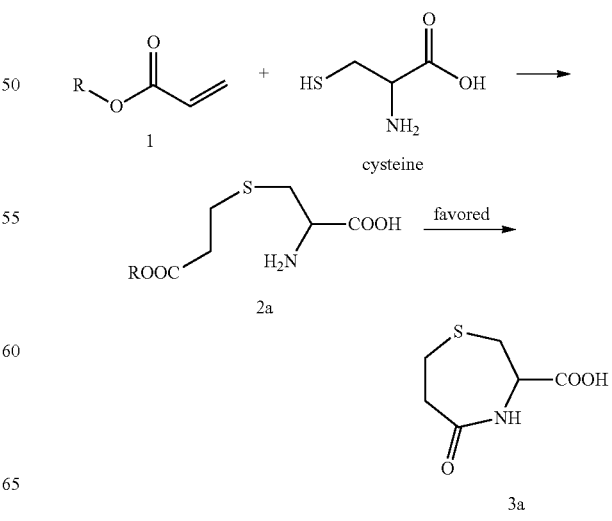

13

-continued

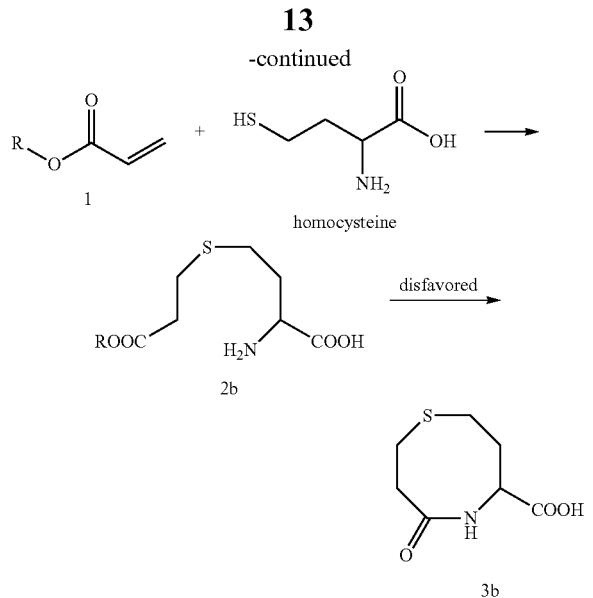

homocysteine

Cysteine (Cys) and homocysteine (Hcy) are structurally related, differing in the presence of a single extra methylene group in the side chain of Hcy. An analogous thioether (2b) is generated from Hcy (Khatik, Org. Lett. 2006, 8, 2433-2436). However, the intramolecular cyclization reaction to form an eight-membered ring (3b) is kinetically disfavored relative to the seven-membered ring as in the case of Cys, i.e., homocysteine's cyclization rate is expected to be less than cysteine's cyclization rate.

To achieve highly selective detection of GSH over Cys and Hcy, one would need to overcome the formidable challenge of favoring formation of a larger 12-membered ring over a 7- or 8-membered ring. It has been reported that cetyltrimethylammonium bromide (CTAB) micelles can catalyze the intramolecular ring closure of larger rings, reversing the expected kinetics based on ring size (Wei et al., Langmuir, 1991, 7, 1336-1339). GSH is capable of binding to the surface of cationic CTAB micelles (Huang et al., Langmuir, 2005, 23, 1518-1522).

Disclosed herein are embodiments of probes that can be used to selectively detect GSH or Cys, as well as methods of making and using the probes. Some embodiments of the probes are suitable for detecting GSH or Cys in biological media.

IV. PROBES

Probes useful for selective detection of biological thiols are disclosed. Some embodiments of the disclosed probes undergo long-wavelength (e.g., 550-700 nm) emission when excited, making them suitable for selectively detecting thiols in biological samples (e.g., blood, plasma, urine, or products or components thereof). The disclosed probes include a fluorophore moiety and a cyclization moiety capable of undergoing a condensation-cyclization reaction with a compound comprising a thiol group and an amino group. Prior to reaction, the probe is colorless and non-fluorescent. After cyclization occurs, the cyclization moiety and thiol-containing compound are eliminating, thereby releasing the fluorophore. The released fluorophore may appear colored in solution. In some embodiments, the probes undergo a conjugate addition and micelle-catalyzed large-membered ring formation/elimination sequence.

Embodiments of the disclosed probes have a chemical structure according to general formula I:

14

(I)

where each bond depicted as "- - - - -" is a single or double bond as needed to satisfy valence requirements; $R^1$, $R^3$-$R^6$ and $R^8$ independently are hydrogen, hydroxyl, thiol, lower alkyl, carboxyalkyl, amino, alkoxy, or halogen; $R^2$ is an α,β-unsaturated aliphatic ester; $R^7$ is oxygen, sulfur, hydrogen, hydroxyl, thiol, lower alkyl, carboxyalkyl, amino, alkoxy, or halogen, or $R^7$ and $R^8$ together form a cycloalkyl or aryl; $X^1$ is $CH_2$, S, NH, O, Se, $Si(CH_3)_2$, $Ge(CH_3)_2$, $Sn(CH_3)_2$, or $C(CH_3)_2$; and $X^2$ is CH, $CH_2$, N, NH, or $CR^9$ where $R^9$ is aryl. $R^2$ is a cyclization moiety capable of reacting with a compound comprising a thiol group and an amino group.

In some embodiments, $X^1$ is O or S, and $R^7$ is O or S, or $R^7$ and $R^8$ together form an aryl ring. In one embodiment, $R^2$ is an acrylate ester, $X^1$ is O or S, and $R^7$ is O or S, or $R^7$ and $R^8$ together form an aryl ring. In another embodiment, $R^1$ and $R^3$-$R^6$ independently are H or lower alkyl, $X^1$ is O or S, and $R^7$ is O or S, or $R^7$ and $R^8$ together form an aryl ring. In one example, $R^1$ is lower alkyl and $R^3$-$R^6$ are H. In another embodiment, $X^1$ is O or S, $R^7$ is O or S, and $R^8$ is H. In yet another embodiment, $X^1$ is O, $X^2$ is N or $CR^9$, $R^1$ is lower alkyl or H, $R^2$ is an acrylate ester, $R^3$-$R^6$ are H, and $R^7$ is O and $R^8$ is H, or $R^7$ and $R^8$ together form an aryl ring.

In some embodiments, the probe has a structure according to general formula IA where $R^7$ is O or S, and $X^2$ is CH, $CH_2$, N, or NH.

(IA)

In one embodiment, $R^2$ is an acrylate ester. In another embodiment, $X^2$ is CH or N, and $R^7$ is O. In yet another embodiment, $R^2$ is an acrylate ester, $X^2$ is CH or N, and $R^7$ is O. In still another embodiment, $R^2$ is an acrylate ester, $R^7$ is O, $X^1$ is O, and $X^2$ is CH or N. In another embodiment, $R^2$ is an acrylate ester, $R^7$ is O, $X^1$ is O, $X^2$ is CH or N, and $R^1$, $R^3$-$R^6$, and $R^8$ independently are H or lower alkyl. In one embodiment, $R^2$ is an unsubstituted acrylate ester, $X^1$ is O, $X^2$ is N, $R^7$ is O, and $R^1$, $R^3$-$R^6$, and $R^8$ are H (i.e., "probe 8").

Probe 8

In some embodiments, $R^7$ and $R^8$ together form an aryl ring, $X^2$ is $CR^9$, and the probe is a seminaphthofluorescein (SNF) with a chemical structure according to general formula II:

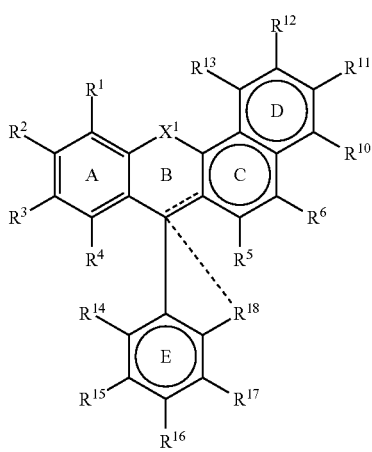

(II)

where " ----- " indicates a single or double bond as needed to satisfy valence requirements and "------" indicates an optional single bond; $X^1$ and $R^1$-$R^6$ are as previously defined; $R^2$ and $R^{11}$ independently are an α,β-unsaturated aliphatic ester; $R^{10}$, $R^{12}$, and $R^{13}$ independently are hydrogen, hydroxyl, thiol, lower alkyl, carboxyalkyl, amino, alkoxy, or halogen; $R^{14}$-$R^{17}$ independently are hydrogen, alkyl, acyl, carboxyl, nitro, amino, alkyl amino, or —$SO_3H$; and $R^{18}$ is hydrogen, hydroxyl, lower alkyl, lower alkoxy, —$SO_3H$ or —$COOR^{19}$ where $R^{19}$ is hydrogen or lower alkyl and the bond depicted as " ----- " in ring B is a double bond, or $R^{18}$ is one or more atoms forming a ring system with rings B and E and the bond depicted as " ----- " in ring B is a single bond. $R^2$ and $R^{11}$ are cyclization moieties capable of reacting with a compound comprising a thiol group and an amino group.

In one embodiment, each of $R^2$ and $R^{11}$ is an acrylate ester. In another embodiment, each of $R^2$ and $R^{11}$ is an acrylate ester, and $R^{18}$ is —COOH or $R^{18}$ is —C(O)O— and forms a ring system with rings B and E. In yet another embodiment, each of $R^2$ and $R^{11}$ is an acrylate ester, $R^1$, $R^3$-$R^6$, $R^{10}$ and $R^{12}$-$R^{17}$ independently are H or lower alkyl, and $R^{18}$ is —COOH or $R^{18}$ is —C(O)O— and forms a ring system with rings B and E. In still another embodiment, $X^1$ is O, each of $R^2$ and $R^{11}$ is an acrylate ester, $R^1$, $R^3$-$R^6$, $R^{10}$ and $R^{12}$-$R^{17}$ independently are H or lower alkyl, and $R^{18}$ is —COOH or $R^{18}$ is —C(O)O— and forms a ring system with rings B and E. In another embodiment, each of $R^2$ and $R^{11}$ is an acrylate ester, $R^1$ is lower alkyl, $R^3$-$R^6$, $R^{10}$ and $R^{12}$-$R^{17}$ are H, and $R^{18}$ is —COOH or $R^{18}$ is —C(O)O— and forms a ring system with rings B and E. In one embodiment, $X^1$ is O, each of $R^2$ and $R^{11}$ is an acrylate ester, $R^1$ is methyl, $R^3$-$R^6$, $R^{10}$ and $R^{12}$-$R^{17}$ are H, and $R^{18}$ is —C(O)O— and forms a ring system with rings B and E (i.e., "probe 5").

Probe 5

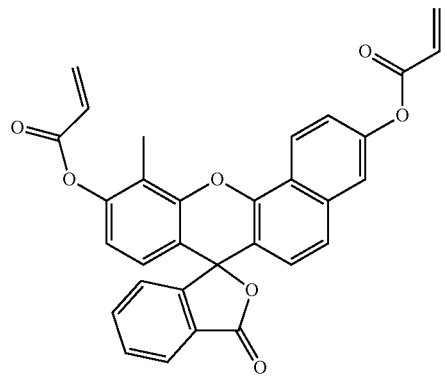

V. THIOL DETECTION AND METHODS OF USE

Figure 2A:
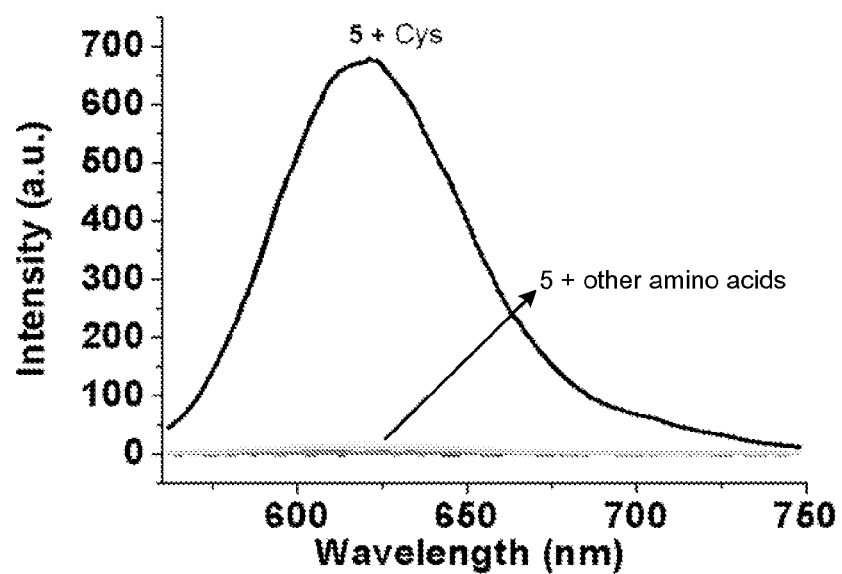
FIGS. 2A-2B show fluorescence spectra ($\lambda_{ex}$=550 nm) obtained from the reaction of probe 5 with cysteine (Cys), homocysteine (Hcy), GSH, and other amino acids in buffered 1.0 mM CTAB; selective detection of cysteine resulted.
Figure 2B:
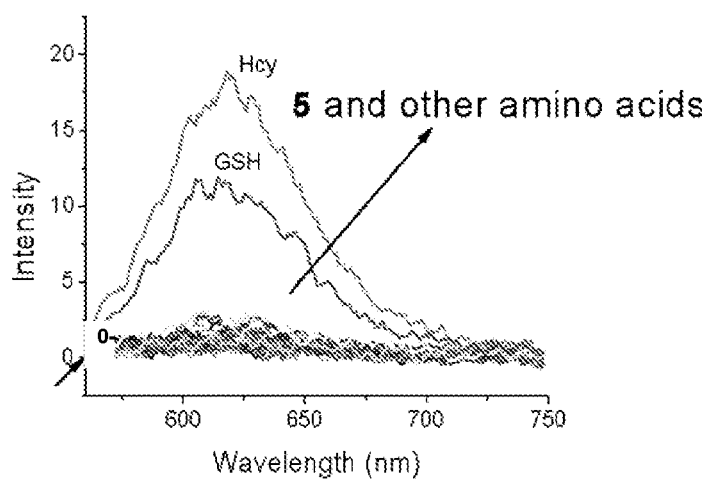
Figure 3:
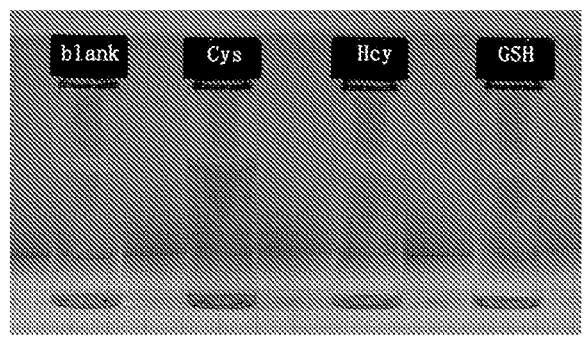
FIG. 3 is a color photograph illustrating selective detection of Cys with probe 5 in 1.0 mM CTAB after 25 minutes.

Without wishing to be bound by any particular theory of operation, probe 5 can be used to selectively detect Cys by the mechanism shown in Scheme 2. Probe 5 is a colorless, non-fluorescent compound. Each acrylate group on the probe undergoes a condensation, cyclization, elimination, and xanthene dye spirolactone-opening sequence with Cys, producing a colored, fluorescent seminaphthofluorescein (see, e.g., FIG. 3). In some embodiments, the probe also reacts with Hcy and GSH to a much lesser extent, but the reaction produces very little fluorescence and no visible color change is seen (FIGS. 2-3). Thus, probe 5 can be used in a time-dependent assay to differentiate between Cys and Hcy/GSH. In some embodiments, probe 5 also is suitable for use as a selective "naked-eye" dosimeter for Cys.

Scheme 2

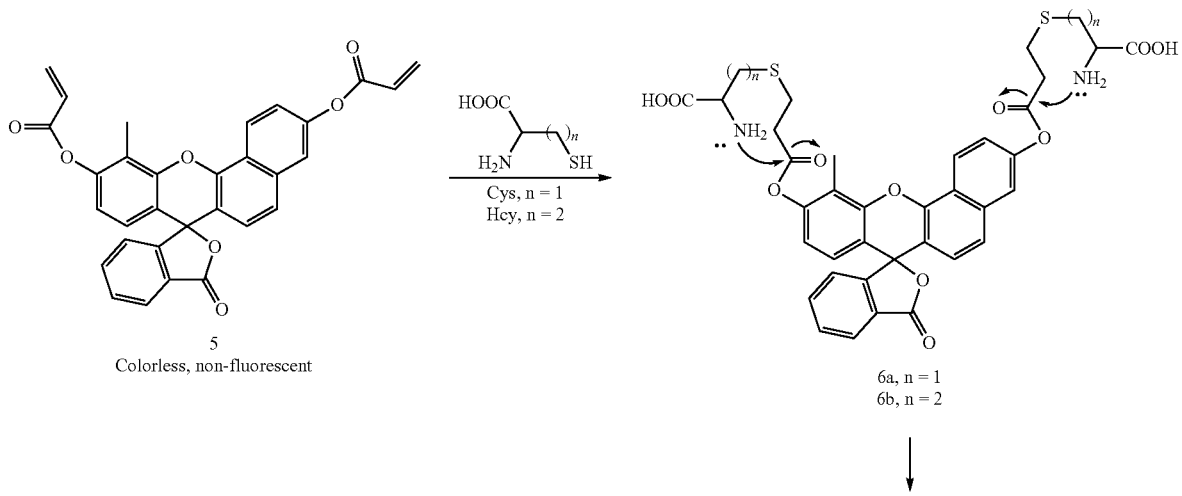

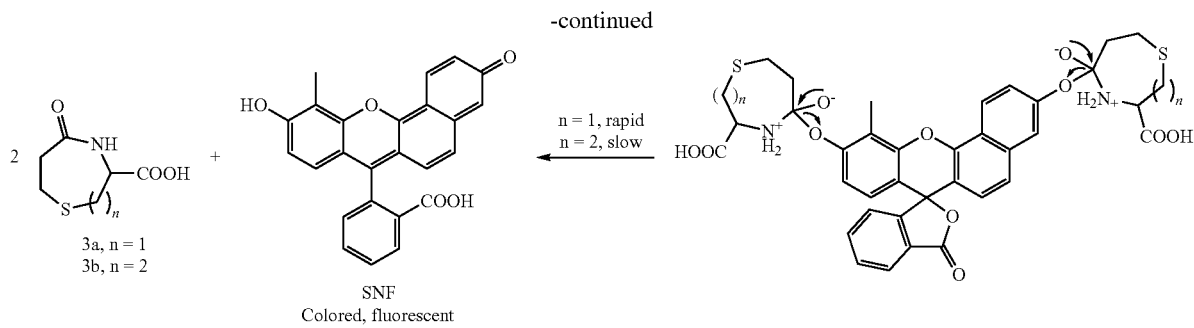

Probe 8, a non-fluorescent compound, undergoes a similar sequence of reactions, releasing highly fluorescent resorufin 7 as shown in Scheme 3. In some solutions, probe 8 selectively detects Cys, and to a lesser extent, Hcy.

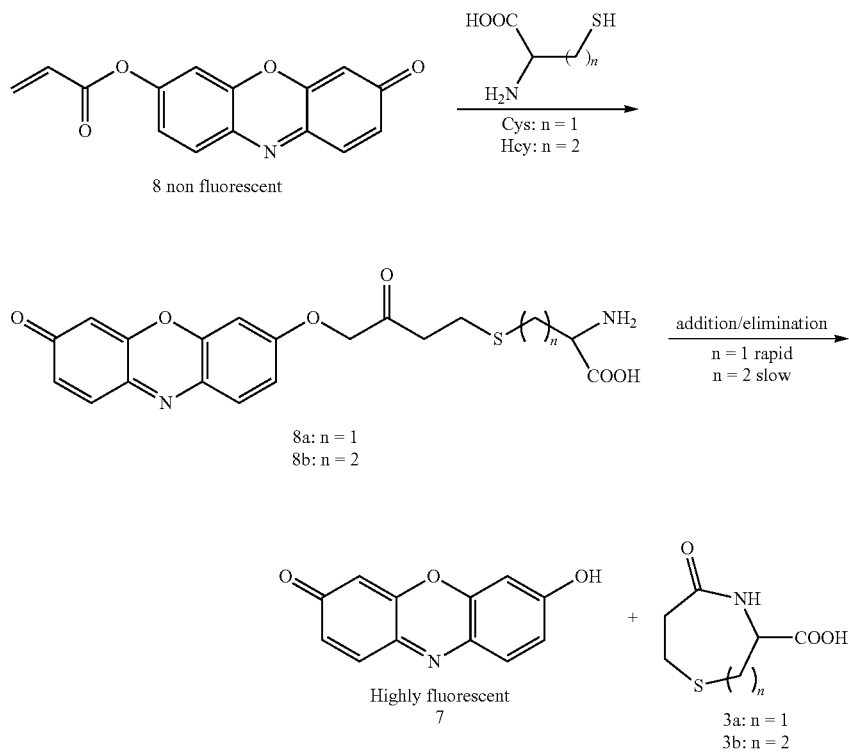

To selectively detect GSH over Cys and Hcy, the formidable challenge of favoring the formation of a larger (12-membered ring in the case of GSH) over a 7- and 8-membered ring (as in 3a and 3b) must be overcome. Inclusion of certain surfactants was discovered to dramatically alter the intrinsic selectivity of probe 8.

Cetyltrimethylammonium bromide (CTAB), a cationic surfactant, forms micelles that can catalyze the intramolecular ring closure of some rings, thereby reversing the expected kinetics based on ring size such that large rings may be closed faster than smaller rings (Wei et al., *Langmuir*, 1991, 7, 1336-1339). GSH has been shown to be capable of binding to the surface of cationic CTAB micelles (Huang et al., *Langmuir*, 2005, 23, 1518-1522).

Because probe 8 is small and substantially planar, it is capable of interacting with the CTAB micelle to facilitate large ring closure and selective detection of GSH. Without wishing to be bound by any particular theory of operation, the mechanism of action involves the conjugate addition of GSH to non-fluorescent probe 8 to generate compound 9, which in turn undergoes an intramolecular cyclization/elimination reaction sequence catalyzed by the CTAB micelle releasing a 12-membered ring 10 and the free resorufin dye 7, and resulting in the recovery of the fluorescence (Scheme 4). High-resolution mass spectrometry demonstrated formation of the 12-membered ring 10 (FIG. 1) and resorufin 7. Other thiols such as Cys and Hcy did not exhibit significant reactions with probe 8 in the presence of CTAB.

Scheme 4

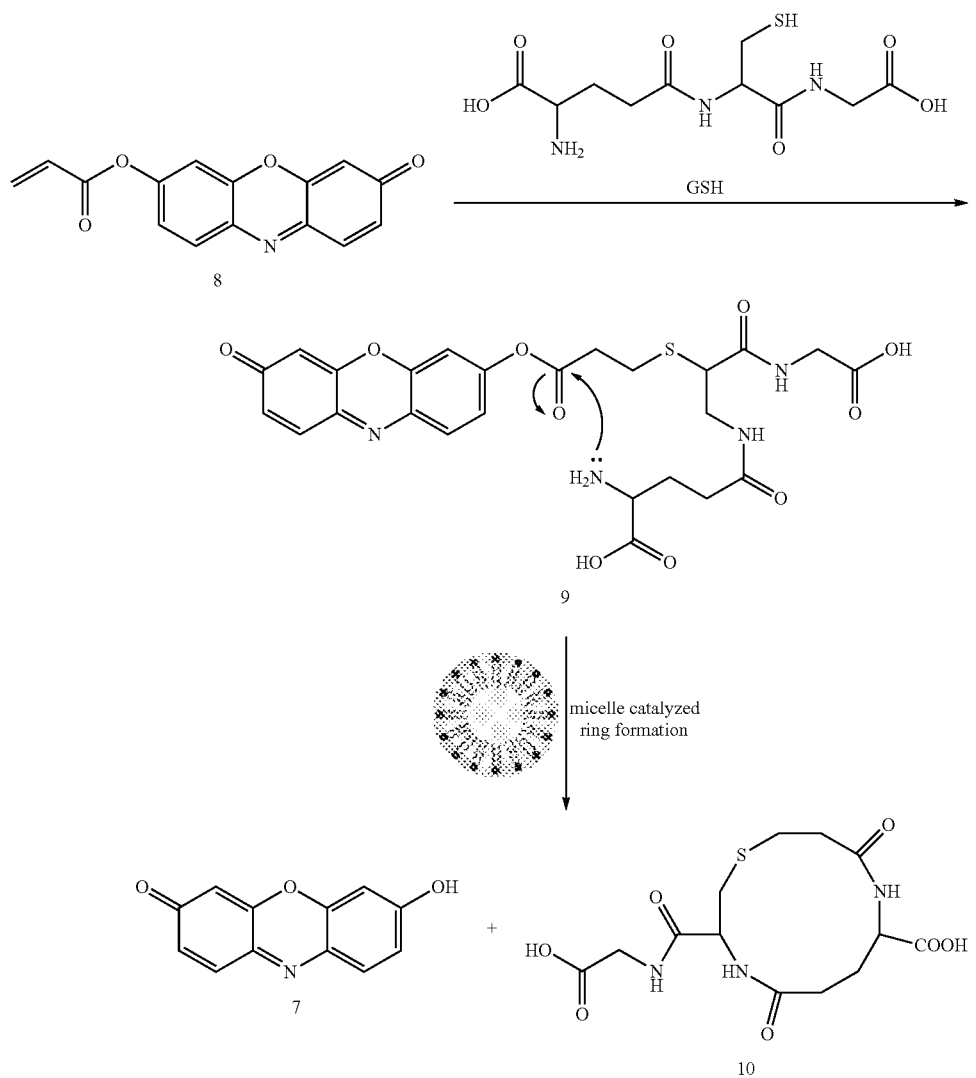

Another cationic surfactant, benzyl-dimethyl-tridecyl-azanium chloride (BC), also produced selective detection of GSH with probe 8. Cys also was detected when BC was included in the solution; however, GSH produced greater fluorescence.

Embodiments of the disclosed probes are suitable for selectively detecting compounds comprising a thiol group and an amino group. Exemplary compounds include the biological thiols Cys, Hcy, and GSH. A sample potentially comprising at least one thiol-containing compound comprising a thiol group and an amino group is combined with a solution comprising a probe according to general formula I. The sample may be a biological fluid, such as blood (e.g., whole blood or a blood product or component, such as plasma) or urine (or a urine product or component). The reaction is allowed to proceed for an effective period of time. An effective period of time is sufficient time for a condensation, cyclization, and elimination reaction to occur if the thiol-containing compound is present in the sample, thereby producing a change in the reaction mixture's absorbance spectrum, fluorescence emission spectrum, or both. In some embodiments, the effective period of time is ≤60 minutes, ≤30 minutes, ≤20 minutes, ≤10 minutes, or ≤5 minutes, such as 10 seconds to 30 minutes, 1-30 minutes, 1-25 minutes, 1-20 minutes, or 1-10 minutes. Presence of the thiol-containing compound is detected by i) comparing a color of the reaction mixture before the reaction to a color of the reaction mixture after the reaction with the compound, (ii) detecting a change in absorbance of the reaction mixture at one or more wavelengths after the reaction has proceeded for the effective period of time, (iii) comparing an absorbance spectrum of the reaction mixture at a first time after combining the sample and the probe to an absorbance spectrum of the reaction mixture after the reaction has proceeded for the effective period of time, (iv) detecting a change in emission of the reaction mixture at one or more wavelengths after the reaction has proceeded for the effective period of time, (v) comparing an emission spectrum of the reaction mixture at a first time after combining the sample and the compound to an emission spectrum of the reaction mixture after the reaction has proceeded for the effective period of time, (vi) or any combination thereof. In the absence of a thiol-containing compound, no change is detected.

A change in the probe's absorbance spectrum may be detected by obtaining an absorbance spectrum, by measuring absorbance at an appropriate wavelength, or by visually detecting a color change (i.e., with the naked eye). A change in the probe's fluorescence spectrum may be detected by obtaining a fluorescence emission spectrum, or by measuring fluorescence intensity at an appropriate wavelength. Absorbance and/or fluorescence changes over time may be measured.

In certain embodiments, a concentration of a thiol-containing compound in a sample may be determined. For example, the concentration of Cys or GSH may be determined. A standard curve is be prepared by combining a probe according to formula I with solutions comprising known amounts of a thiol-containing compound. After an effective period of time, absorbance and/or fluorescence is measured at an appropriate wavelength. In some examples, when probe 8 was used, the effective period of time was less than 1 minute, 2 minutes, 8 minutes, 10 minutes, 20 minutes, or 60 minutes, and fluorescence emission was measured at 585-590 nm ($\lambda_{ex}$=565 nm); an absorbance maximum was seen at 585-590 nm. In certain examples when probe 5 was used, the effective period of time was 25 minutes, and a fluorescence maximum was seen at 615-620 nm ($\lambda_{ex}$,=550 nm). A sample potentially comprising the thiol then is combined with the probe under the same conditions (solution composition, pH, time, temperature), and absorbance and/or fluorescence then is measured and compared to the calibration curve to determine the thiol concentration in the sample.

In some embodiments, the sample is buffered to a pH of 5.5-8.0, such as a pH of 6.0-7.5. Fluorescence may develop more quickly at higher pH; however, selectivity may be enhanced at a lower pH. In certain embodiments, the sample was buffered to a pH of 6 when detecting GSH in biological fluids.

In some examples, the sample comprises sulfhydryl-containing compounds other than Cys, Hcy, and/or GSH, and/or exhibits significant absorbance, fluorescence, and/or scatter in the visible wavelength region. In certain embodiments, the sample is a biological fluid, such as blood, a blood product or component (e.g., plasma), urine, or a urine product or component.

In one embodiment, the sample comprises plasma, and the method further includes combining the plasma with a reducing agent (e.g., triphenylphosphine or TCEP (tris-(2-carboxyethyl)-phosphine)), and removing proteins from the plasma. Proteins may be removed, for example, by precipitation. The plasma may be diluted (e.g., to a concentration of 5-20%, such as to 10%) with a buffer. In one example, a 50 mM phosphate buffer, pH 6.0 was used. A probe according to general formula I is combined with the reduced, deproteinized plasma. Presence of a thiol is determined by detecting a change in the reaction mixture's absorbance spectrum, emission spectrum, or both.

In another embodiment, the sample comprises whole blood. Whole blood is spotted onto absorbent paper and dried. Thiols are extracted from the dried blood spot. In one example, a phosphate buffer (100 mM, pH 6.0) was used to perform the extraction. The extract is reduced, e.g., with TCEP or triphenylphosphine. Reduced thiols are isolated by fractionating the reduced extract, such as by gel filtration, to remove proteins and other high molecular weight molecules. In one example, a desalting column comprising a cross-linked dextran gel capable of fractionating globular proteins having a molecular weight of 1000-5000 Daltons (Sephadex® G-25, GE Healthcare) was used with 100 mM phosphate buffer as an eluent. An isolated fraction is combined with a probe according to general formula I. Presence of a thiol is determined by detecting a change in the reaction mixture's absorbance spectrum, emission spectrum, or both.

In some embodiments, Cys is selectively detected by combining a sample potentially comprising Cys with a probe according to formula IA in the absence of a cationic surfactant. In certain embodiments, Cys is selectively detected with probe 8. The reaction may be performed at pH of 6-7.5 for 1-60 minutes. The sample and/or probe may be provided in a solution comprising an anionic or non-ionic surfactant. For example, Triton® X-100 (polyethylene glycol tert-octylphenyl ether) may increase probe selectivity for Cys and/or may increase the rate at the reaction occurs, e.g., 10-15 minutes. Cys is detected by detecting a change in the reaction mixture's absorbance spectrum, emission spectrum, or both. When probe 8 is used, fluorescence may be produced with an excitation wavelength of 565 nm. Fluorescence is detected by measuring fluorescence intensity at an emission wavelength of 580-590 nm, or by obtaining a fluorescence emission spectrum. In some examples, Cys can be detected visually by observing development of a pink color in the reaction mixture.

Alternatively, Cys can be selectively detected by combining a sample potentially comprising Cys with a probe according to formula II. In certain embodiments, probe 5 is used to selectively detect Cys. The reaction may be performed at a pH of 6-7.5 for 1-30 minutes. The sample and/or probe may be provided in a solution comprising a surfactant, e.g., a cationic surfactant such as CTAB. Cys is detected by detecting a change in the reaction mixture's absorbance spectrum, emission spectrum, or both. When probe 5 is used, fluorescence may be produced with an excitation wavelength of 550 nm. Fluorescence is detected by measuring fluorescence intensity at a wavelength of 615-635 nm, or by obtaining a fluorescence emission spectrum. In some examples, Cys can be detected visually by observing development of a pink color in the reaction mixture.

GSH can be selectively detected by combining a sample potentially comprising GSH with a probe according to formula IA in the presence of a cationic surfactant. In some embodiments, GSH is selectively detected with probe 8. Suitable cationic surfactants include CTAB and BC. The reaction may be performed at a pH of 6-7.5 for 0-30 minutes. GSH also may be selectively detected by probe 8 in certain solvents, such as a polar aprotic solvent. For example, probe 8 selectively detected GSH in a 1:1 solution of DMSO:$H_2O$ (pH 7.4). GSH is detected by detecting a change in the reaction mixture's absorbance spectrum, emission spectrum, or both. When probe 8 is used, fluorescence may be produced with an excitation wavelength of 565 nm. Fluorescence is detected by measuring fluorescence intensity at an emission wavelength of 580-590 nm, or by obtaining a fluorescence emission spectrum. In some embodiments, GSH can be detected visually by observing development of a pink color in the solution.

VI. PROBE SYNTHESIS

In some embodiments, a probe having a structure according to general formula IA is synthesized in a one-step reaction as shown below in Scheme 5. Resorufin, or a resorufin analog, is combined with an acryloyl salt, such as an acryloyl chloride, in the presence of dichloromethane and triethylamine to produce the acrylate resorufin analog. $R^1$ and $R^3$-$R^8$ are as previously defined.

Scheme 5

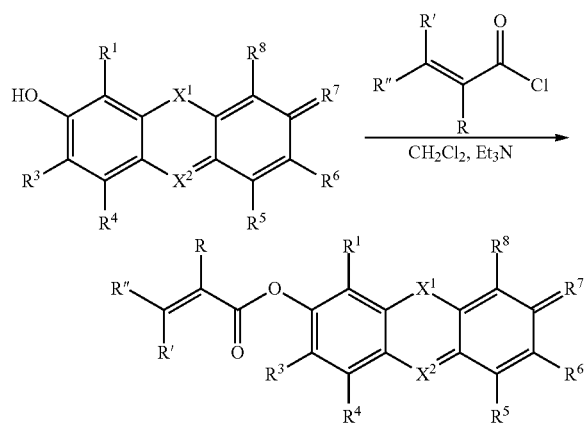

R, R', R'' independently are hydrogen, halogen, hydroxyl, lower alkoxy, lower aliphatic, or aryl In certain embodiments, a probe having a structure according to general formula II is synthesized as shown below in Scheme 6. A hydroxybenzophenone derivative is prepared by reacting a 1,3-dihydroxyphenyl derivative with a 2-benzofuran-1,3-dione derivative with aluminum chloride. The hydroxybenzophenone derivative and a 1,8-naphthalene derivative are condensed by reaction with methanesulfonic acid to produce a seminaphthofluorescein (SNF) derivative. The SNF derivative is then reacted with an acryloyl salt in the presence of triethylamine and dichloromethane to produce the acrylate SNF derivative. $R^1$, $R^3$-$R^6$, $R^{10}$, and $R^{12}$-$R^{17}$ are as previously defined.

Scheme 6

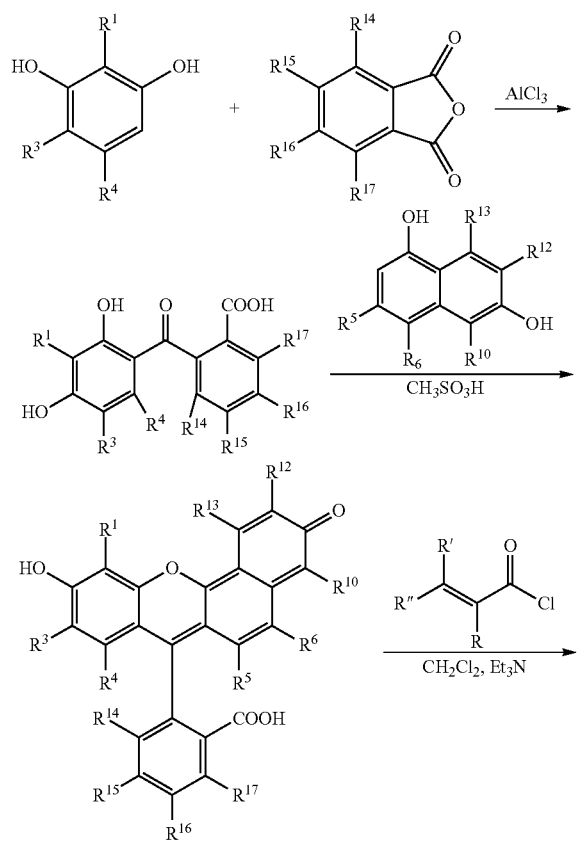

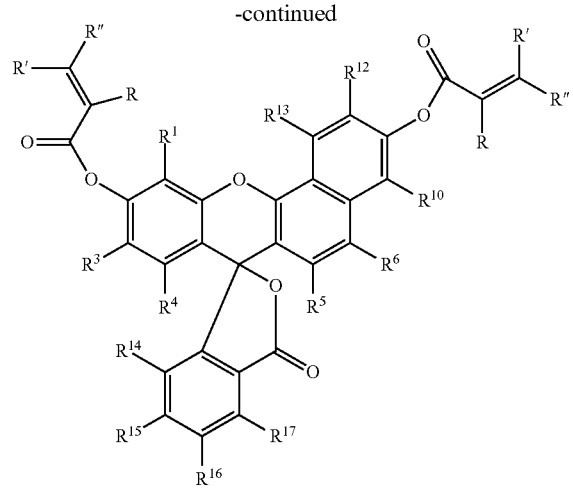

R, R', R'' independently are hydrogen, halogen, hydroxyl, lower alkoxy, lower aliphatic, or aryl

VII. KITS

Kits are also a feature of this disclosure. Embodiments of the kits include at least one probe as disclosed herein, wherein the probe is suitable for selectively detecting one or more thiol-containing compounds, particularly one or more compounds including a thiol group and an amino group (e.g., cysteine, homocysteine, glutathione). In some embodiments, the kit further includes a buffer solution at physiologic pH. In certain embodiments, the buffer is a phosphate buffer at pH 6-7.5, such as a 20-50 mM phosphate or HEPES buffer at pH 7.4 or a 50-100 mM phosphate buffer at pH 6.0. The probe may be dissolved in the buffer, or the probe may be included in a dry form and the user can combine the probe and the buffer solution at or before the time of use. In some embodiments, the buffer solution further includes a surfactant. The kits also may include one or more containers, such as a disposable test tube or cuvette, in which the detection can be performed. In some embodiments, an amount of the probe effective to undergo a detectable change in color and/or a detectable change in the fluorescence emission spectrum when reacted with the at least one compound is premeasured into the disposable containers. The kits may further include instructions for performing the detection. In some embodiments, the kits include control samples of thiol-containing compounds, e.g., cysteine, homocysteine, and/or glutathione. Typically the control samples are provided in solid form.

VIII. EXAMPLES

Materials and Instruments

All chemicals were purchased from Sigma-Aldrich or Acros and used without further purification. In all experiments enantiomerically pure natural amino acids were used except for Hcy, which was used as the racemate. $^1$H-NMR and $^{13}$C-NMR spectra were recorded on a Bruker AMX-400 NMR spectrometer, using TMS as an internal standard. ESI-HRMS (high-resolution mass spectrometry) spectra were obtained on a Thermo Electron LTQ Orbitrap hybrid mass spectrometer. UV-visible spectra were collected on a Cary 50 UV-Vis spectrophotometer. Fluorescence spectra were collected on a Cary Eclipse (Varian, Inc.) fluorescence spectrophotometer with slit widths set at 5 nm for both excitation and emission, respectively. The high voltage of the fluorescence spectrophotometer was set at 500 V for probe 8. The pH measurements were carried out with an Orion 410A pH meter.

Example 1

Synthesis of Probe 5

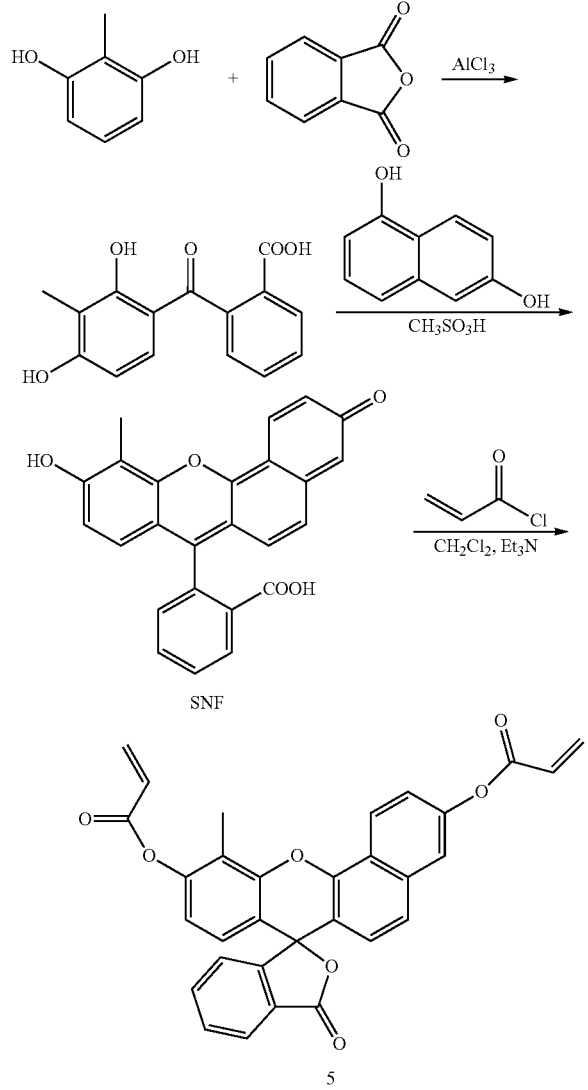

SNF was synthesized in two steps according to a published method (Chang et al., *Proc. Natl. Acad. Sci. USA*, 2004, 101, 1129-1134). $^1$H NMR (CDCl$_3$, 400 MHz), δ (ppm): 8.44 (d, 1H, J=9.2 Hz), 8.04 (d, 1H, J=7.2 Hz), 7.74 (m, 2H), 7.30 (d, 1H, J=9.2 Hz), 7.26 (dd, 1H, J$_1$=2.4 Hz, J$_2$=9.2 Hz), 7.19 (d, 1H, J=7.6 Hz), 7.12 (s, 1H), 6.62 (m, 2H), 6.51 (d, 1H, J=8.8 Hz), 2.51 (s, 3H). ESI-FTMS m/z=395.0923 [M−H]$^−$, calc. 395.0919 for C$_{25}$H$_{15}$O$_5$.

To a solution of SNF (120 mg, 0.30 mmol) and triethylamine (2 equiv) in 10 mL of anhydrous CH$_2$C$_{12}$, acryloyl chloride (2.5 eq, mixed with 5 mL of CH$_2$C$_{12}$) was added dropwise at 0° C. After stirring at this temperature for 90 minutes, the resulting mixture was allowed to warm to room temperature and stirred overnight. The mixture was then diluted with CH$_2$Cl$_2$ (25 mL), washed with water (12 mL×3) and dried over anhydrous Na$_2$SO$_4$. The solvent was removed by evaporation to get crude product as yellow solids, which was then purified by flash column chromatography (silica gel, CHCl$_3$/EtAC 100:6) to get 4 as light yellow solids (99 mg, 65% yield). $^1$H NMR (CDCl$_3$, 400 MHz), δ (ppm): 8.58 (d, 1H, J=9.2 Hz), 8.07 (d, 1H, J=8.0 Hz), 7.66 (m, 3H), 7.46 (m, 2H), 7.16 (d, 1H, J=6.4 Hz), 6.83 (m, 2H), 6.76 (d, 1H, J=8.4 Hz), 6.70 (br s, 1H), 6.66 (br s, 1H), 6.41 (dd, 1H, J$_1$=1.6 Hz, J$_2$=10.4 Hz), 6.37 (dd, 1H, J$_1$=1.6 Hz, J$_2$=10.4 Hz), 6.08 (m, 2H), 2.51 (s, 3H). $^{13}$C NMR (CDCl$_3$, 100 MHz), δ 169.52, 164.57, 164.05, 153.67, 150.31, 150.15, 149.84, 146.93, 135.38, 135.27, 133.49, 133.22, 130.09, 127.90, 127.49, 125.31, 124.83, 124.28, 123.96, 123.60, 122.09, 121.99, 119.45, 118.88, 118.15, 116.49, 112.42, 82.92, 9.87. ESI-FTMS m/z=505.1308 [M+H]$^+$, calc. 505.1287 for C$_{31}$H$_{21}$O$_7$.

Example 2

Selective Detection of Cysteine with Probe 5

Probe 5 (10 μM) was combined with 1 equivalent of Cys, Hcy, GSH, leucine, proline, arginine, histidine, valine, methionine, threonine, glutamine, alanine, aspartic acid, norleucine, isoleucine, lysine, tryptophan, tyrosine, phenylalanine, cystine, or homocystine for 25 minutes in 1.0 mM CTAB buffered at pH 7.4 (HEPES buffer, 20 mM). Fluorescence spectra were obtained at an excitation wavelength of 550 nm. As shown in FIG. 2A, only Cys resulted in significant fluorescence. A minor amount of fluorescence was obtained following reaction with Hcy and GSH (FIG. 2B), but no significant fluorescence was obtained from the other evaluated compounds. FIG. 3 is a photograph illustrating the visible color change obtained when probe 5 reacted with Cys. No color change was observed with Hcy or GSH.

Example 3

Synthesis of Probe 8

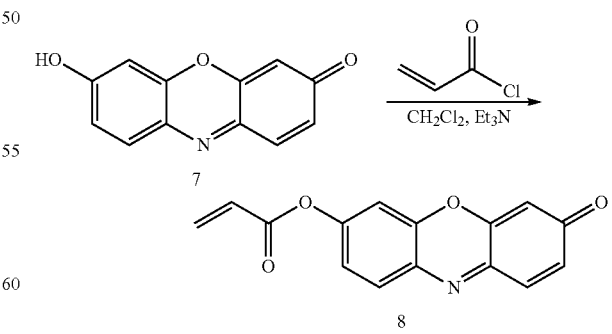

Probe 8 was synthesized in a one-step reaction of resorufin 7 with acryloyl chloride (Scheme 6). To a solution of resorufin (7, 220 mg) and triethylamine (1.5 equiv) in 15 mL of anhydrous CH$_2$Cl$_2$, acryloyl chloride (2.0 equiv in 5 mL of CH$_2$Cl$_2$) was added dropwise at 0° C. After stirring at this temperature for 60 minutes, the resulting mixture was allowed to cool to room temperature and stirred overnight. The mixture was diluted with CH$_2$Cl$_2$ (20 mL), washed with H$_2$O (10 mL×3) and dried over anhydrous Na$_2$SO$_4$. The solvent was removed by evaporation to afford an orange solid (172 mg, 70% yield). $^1$H NMR (CDCl$_3$, 400 MHz), δ (ppm): 7.92 (d, 1H, J=8.7 Hz), 7.59 (d, 1H, J=9.8 Hz), 7.49 (s, 1H), 7.33 (dd, 1H, J$_1$=2.4 Hz, J$_2$=2.5 Hz), 6.83 (dd, 1H, J$_1$=2.0 Hz, J$_2$=2.0 Hz), 6.63 (d, 1H, J=17.2 Hz), 6.49 (m, 1H), 6.24 (s, 1H), 6.22 (d, 1H, J=1.0 Hz). $^{13}$C NMR (CDCl$_3$, 100 MHz), δ 186.48, 163.84, 153.24, 148.87, 147.78, 143.55, 134.85, 134.26, 134.15, 131.22, 131.16, 127.18, 118.82, 109.94, 105.86. ESI-MS m/z=268.0833 [M+H]$^+$, calc. 268.0810 for C$_{15}$H$_{10}$NO$_4$.

Example 4

Detection of Cysteine with Probe 8

Probe 8 (2.5 μM) was combined with thiols (2 equivalents) in phosphate buffer (pH. 7.4, 50 mM). After 20 minutes, absorption and fluorescence ($\lambda_{ex}$=565 nm) spectra were obtained. Fluorescence changes ($\lambda_{em}$=587 nm) over time also were monitored.

Figure 4:
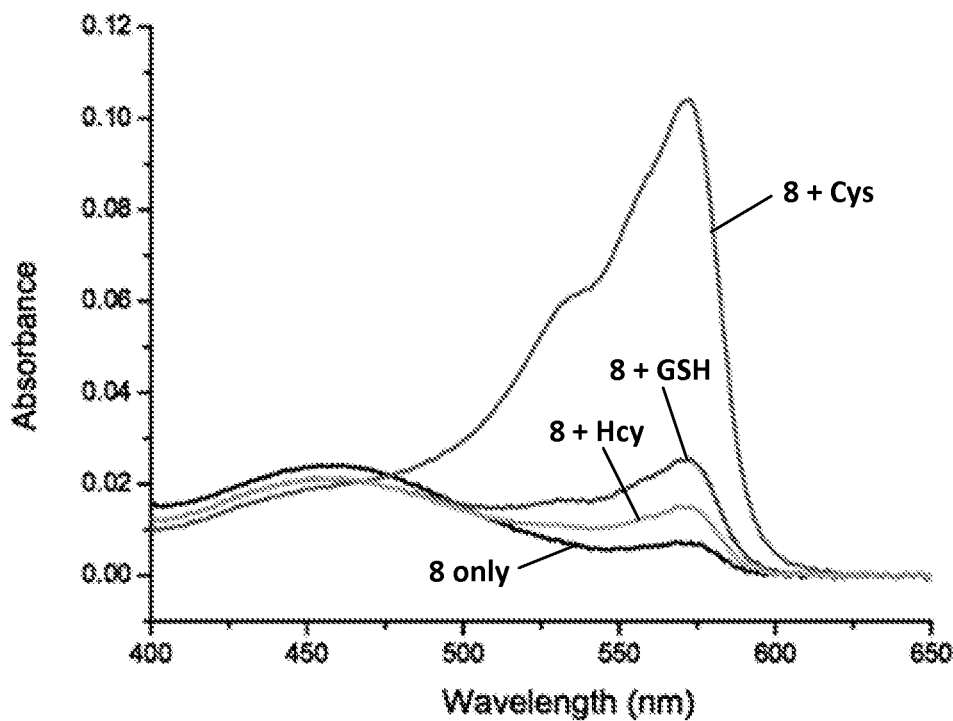
FIG. 4 shows absorption spectra obtained from the reaction of probe 8 with Cys, Hcy, or GSH in phosphate buffer (pH 7.4, 50 mM) after 20 minutes.
Figure 5:
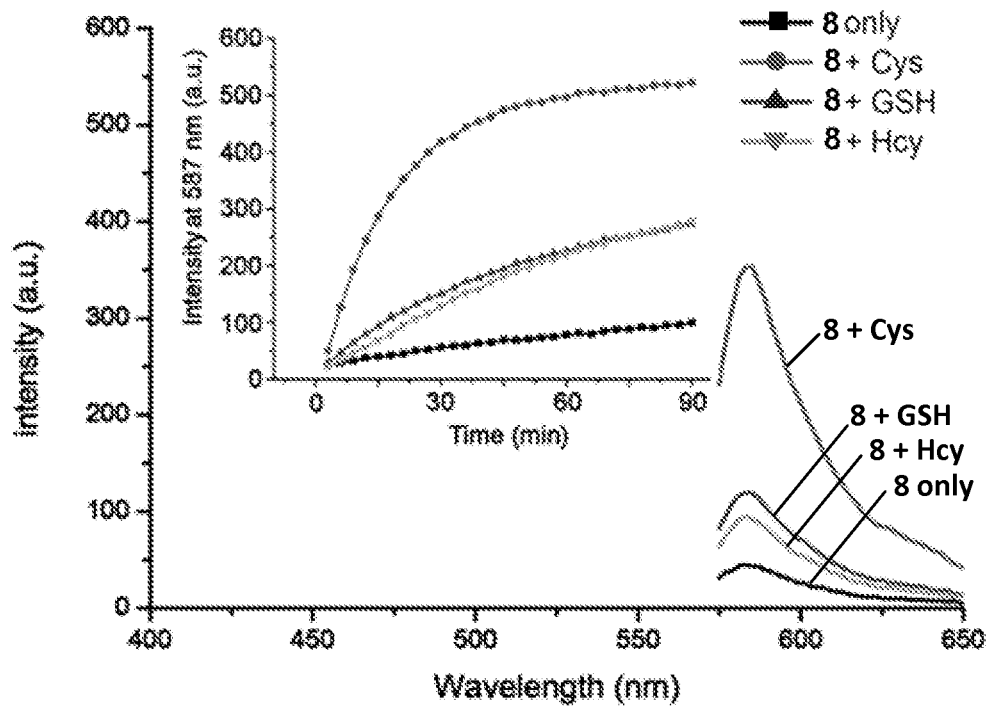
FIG. 5 shows fluorescence spectra ($\lambda_{ex}$=565 nm, $\lambda_{em}$=587 nm) obtained from the reaction of probe 8 with Cys, Hcy, or GSH in phosphate buffer (pH 7.4, 50 mM) after 20 minutes; the time-dependent fluorescence changes also were monitored (inset).

In the phosphate buffer, probe 8 showed excellent selectivity towards Cys due to the kinetically favored 7-membered ring formation. Upon mixing Cys with probe 8, the conjugate addition product 8a is formed, which undergoes a rapid cyclization reaction to produce 3a while releasing the free resorufin (Scheme 3, above). A significant color change and fluorescence enhancement was observed in response to Cys (FIGS. 4, 5). In the case of Hcy, because it has an additional methylene group in its side chain, a kinetically less favored 8-membered ring forms. With GSH, 1,4-addition of thiols to the α,β-unsaturated carbonyl moieties of probe 8 can occur readily; however, the ensuing intramolecular cyclization similar to that of Cys does not proceed in phosphate buffer. No significant color formation or fluorescence response was seen in the case of Hcy or GSH under these conditions (FIGS. 4, 5).

The time course of the fluorescence assay is shown in FIG. 5 (inset). It can be seen that the fluorescence upon reaction with Cys increased with time and reached a plateau after about 90 minutes, whereas for Hcy and GSH the reactions were significantly slower.

Figure 6:
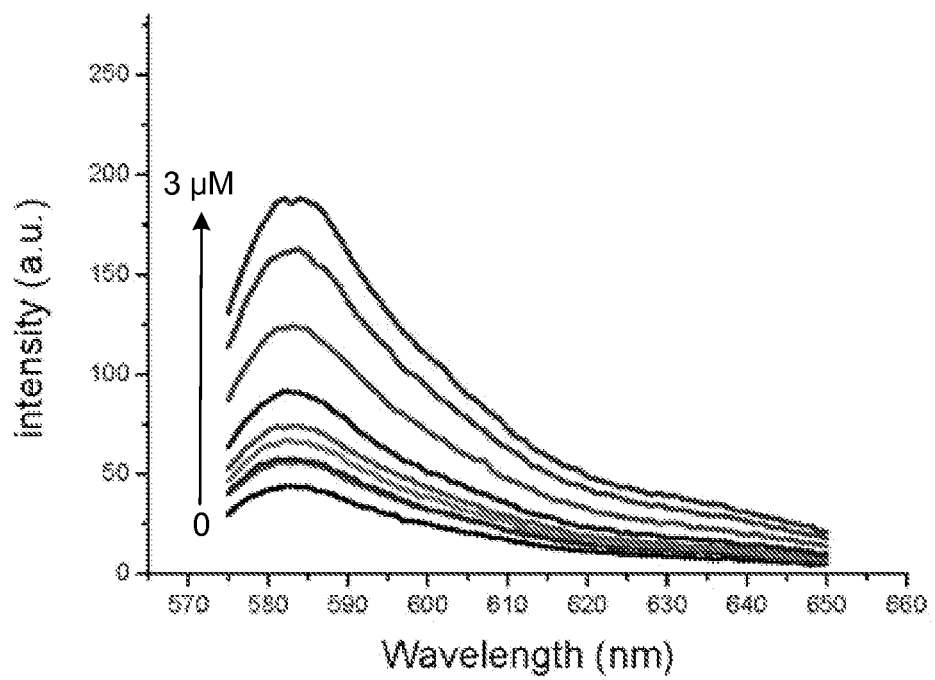
FIG. 6 shows fluorescence spectra obtained from the reaction of probe 8 with varying concentrations of Cys at pH 7.4 (phosphate buffer, 50 mM); reaction time of 60 minutes.
Figure 7:
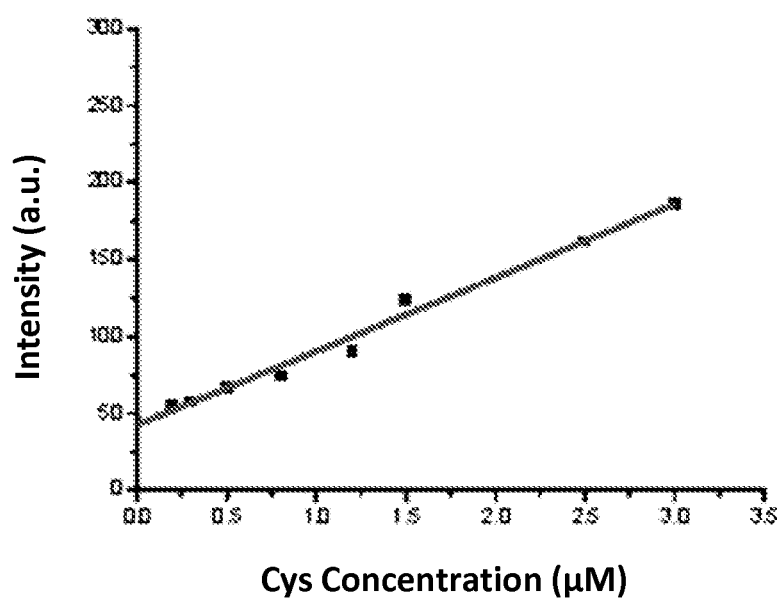
FIG. 7 is a graph illustrating the relationship between fluorescence intensity and Cys concentration when Cys is reacted with probe 8 at pH 7.4 (phosphate buffer, 50 mM); reaction time of 60 minutes.

The sensitivity and linearity of the response of probe 8 towards Cys was also investigated. Various concentrations (0-3 μM) of Cys were combined with probe 8 (2.5 μM) in at pH 7.4 (phosphate buffer, 50 mM), and the reaction was allowed to proceed for 60 minutes. FIG. 6 shows the fluorescence spectra ($\lambda_{ex}$=565 nm) obtained 60 minutes after Cys and probe 8 were combined. FIG. 7 is a graph illustrating the linear increase (correlation coefficient of 0.995) in fluorescence intensity at 593 nm as a function of Cys concentration. Linear response with submicromolar sensitivity was observed, demonstrating that concentrations as low as 0.2 μM Cys can be detected.

Figure 8:
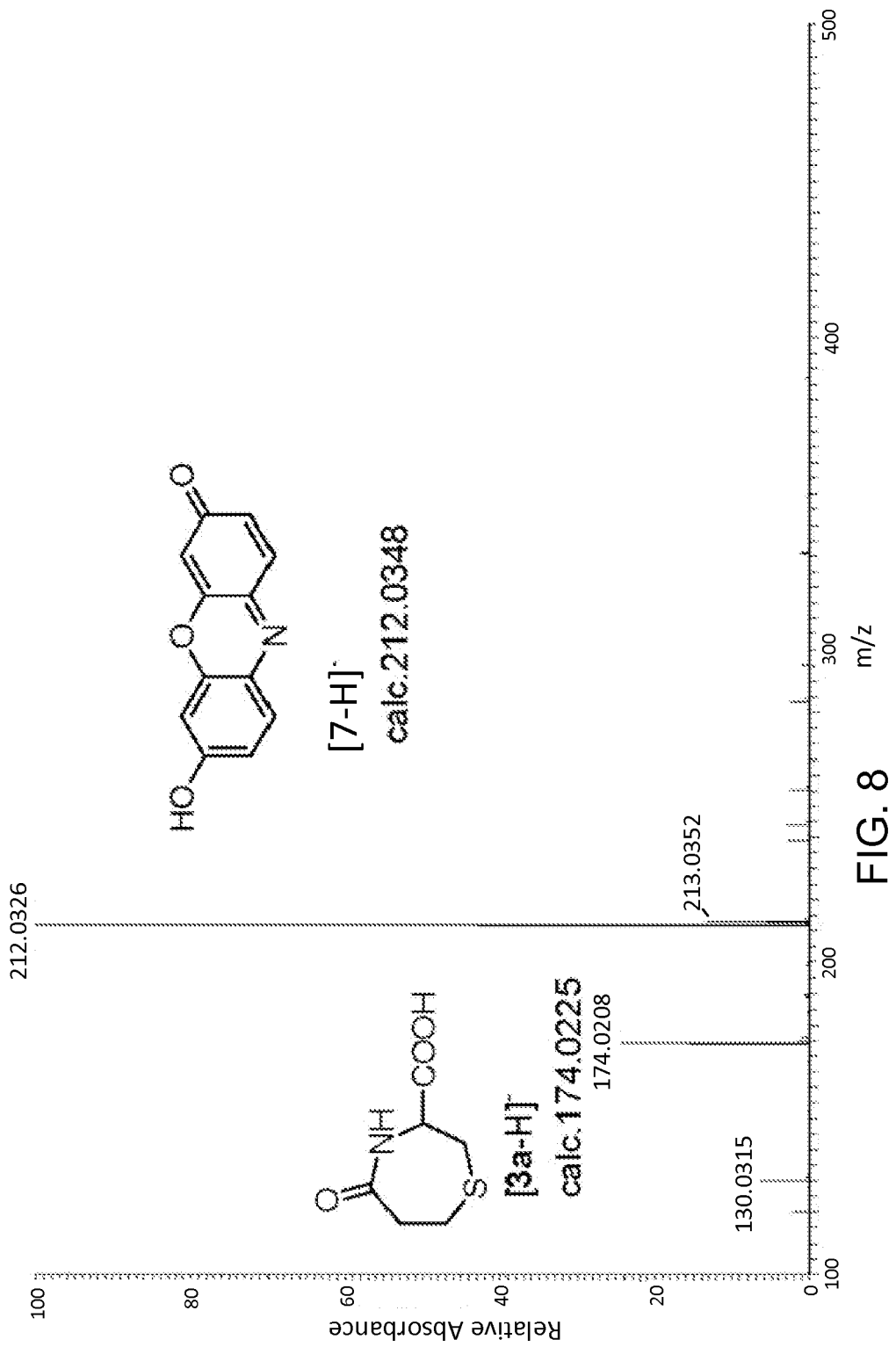
FIG. 8 is a high-resolution mass spectrum demonstrating formation of 3-carboxy-5-oxoperhydro-1,4-thiazepine and release of resorufin when probe 8 is reacted with Cys in phosphate buffer (50 mM, pH 7.4). RT: 0.09; AV: 1; NL: 7.21E7; T: FTMS-pESI Full ms[100.00-500.00].
Figure 9:
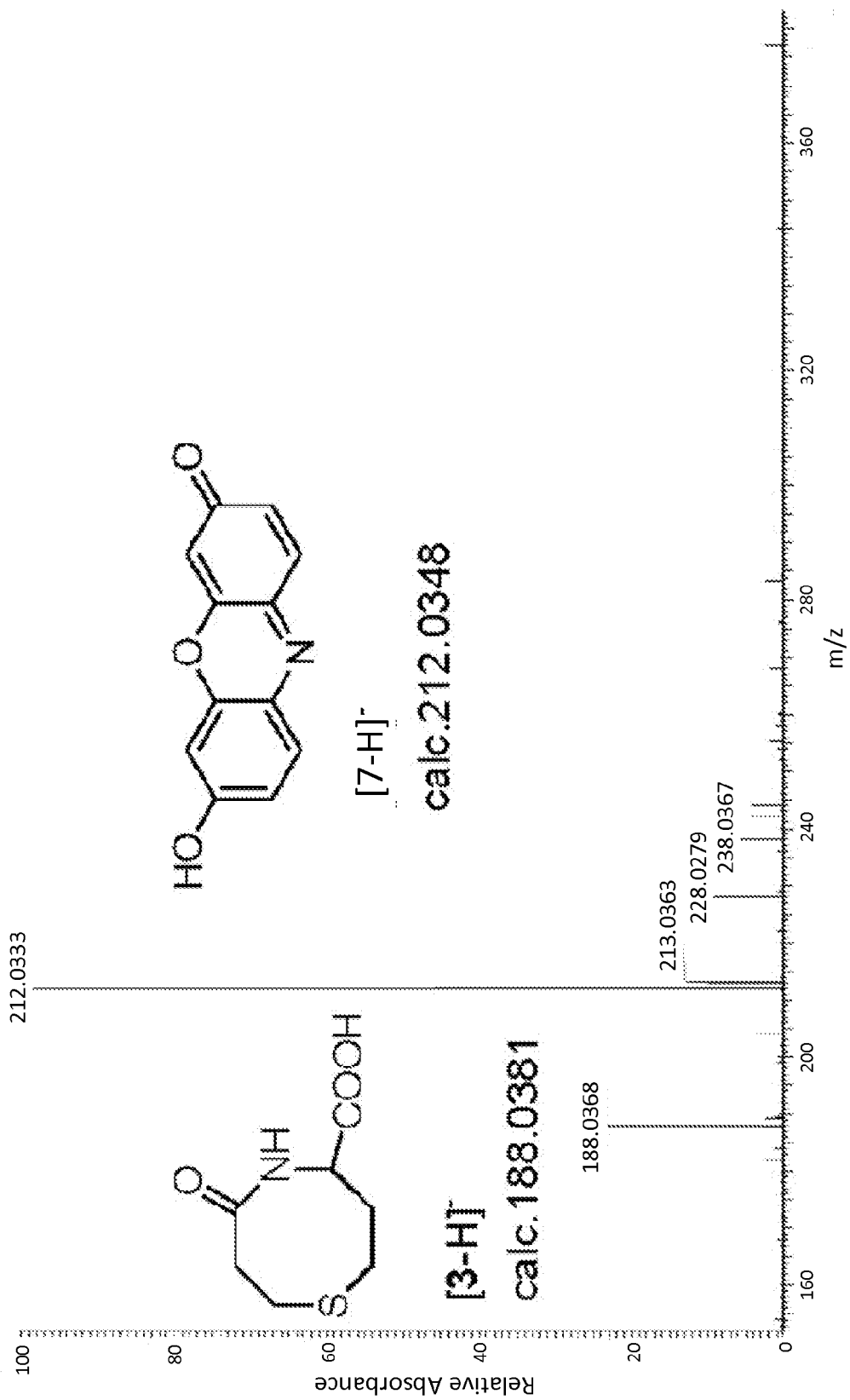
FIG. 9 is a high-resolution mass spectrum demonstrating formation of an 8-membered ring and release of resorufin when probe 8 is reacted with Hcy in phosphate buffer (50 mM, pH 7.4). RT: 0.11-0.21; AV: 7; NL: 7.09E7; T: FTMS—pESI Full ms[100.00-1000.00].

High-resolution mass spectrometry demonstrated the formation of compound 3a (3-carboxy-5-oxoperhydro-1,4-thiazepine) and release of resorufin 7 when probe 8 (20 μM) was combined with Cys (20 μM) in 1:1 MeOH:H$_2$O (FIG. 8). The reaction time was 3 hours. Similarly, compound 3b was formed and resorufin was released when probe 8 (20 μM) was combined with Hcy (20 μM) in 1:1 MeOH:H$_2$O (reaction time=3 hours) (FIG. 9).

To demonstrate the necessity of a free NH$_2$ group, experiments using N-acetyl cysteine (NAC) were performed. Cys and NAC (12.5 μM in phosphate buffer (50 mM, pH=7.4) were added to solutions containing probe 8 (2.5 μM). Absorbance and emission spectra were obtained over a time course of 90 minutes. No significant absorbance or emission was obtained from the reactions including NAC. The results showed that the free NH$_2$ group was required for an intramolecular cyclization and addition/elimination reaction to occur.

Example 5

Effect of CTAB on Selectivity of Probe 8

Figure 10:
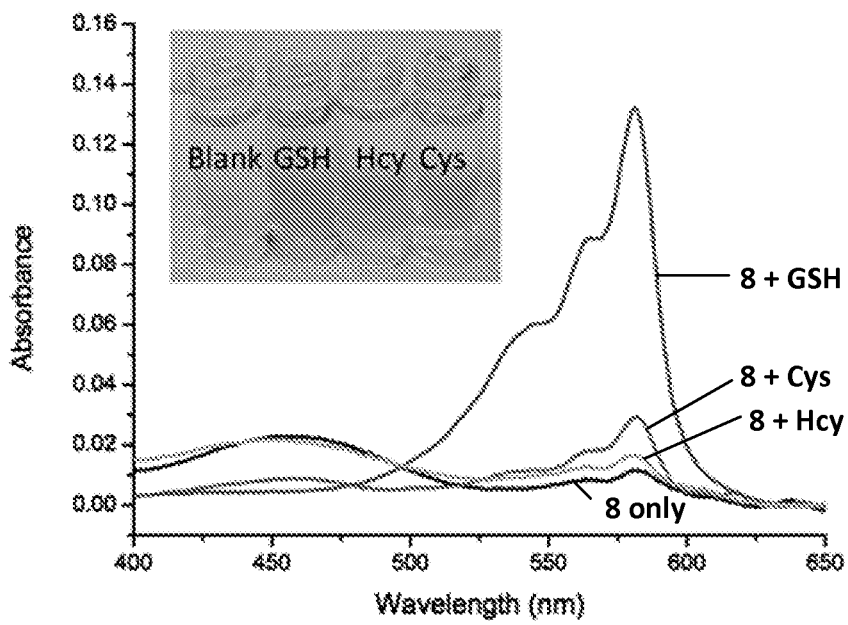
FIG. 10 shows absorbance spectra of probe 8 combined with Cys, Hcy, or GSH in 2.0 mM CTAB buffered at pH 7.4. Inset is a color photograph illustrating selective detection of GSH; the photograph was taken immediately upon the addition of CTAB.

Cys, Hcy, or GSH (2 equivalents) was added to probe 8 (10 μM) in 4 mL phosphate buffer (pH 7.4, 50 mM). CTAB was then added to form a solution containing 2 mM CTAB. A strong pink color formed in the GSH-containing solution immediately upon addition of CTAB. FIG. 10 shows absorbance spectra of probe 8 combined with the thiols. Inset is a color photograph illustrating selective detection of GSH; the photograph was taken immediately upon the addition of CTAB. A strong pink color was obtained immediately upon addition of CTAB in the presence of GSH (inset). Hcy and Cys did not exhibit significant changes under the same conditions. These results indicate that a probe 8-CTAB system can serve as a selective visual inspection dosimeter for GSH.

Figure 1:
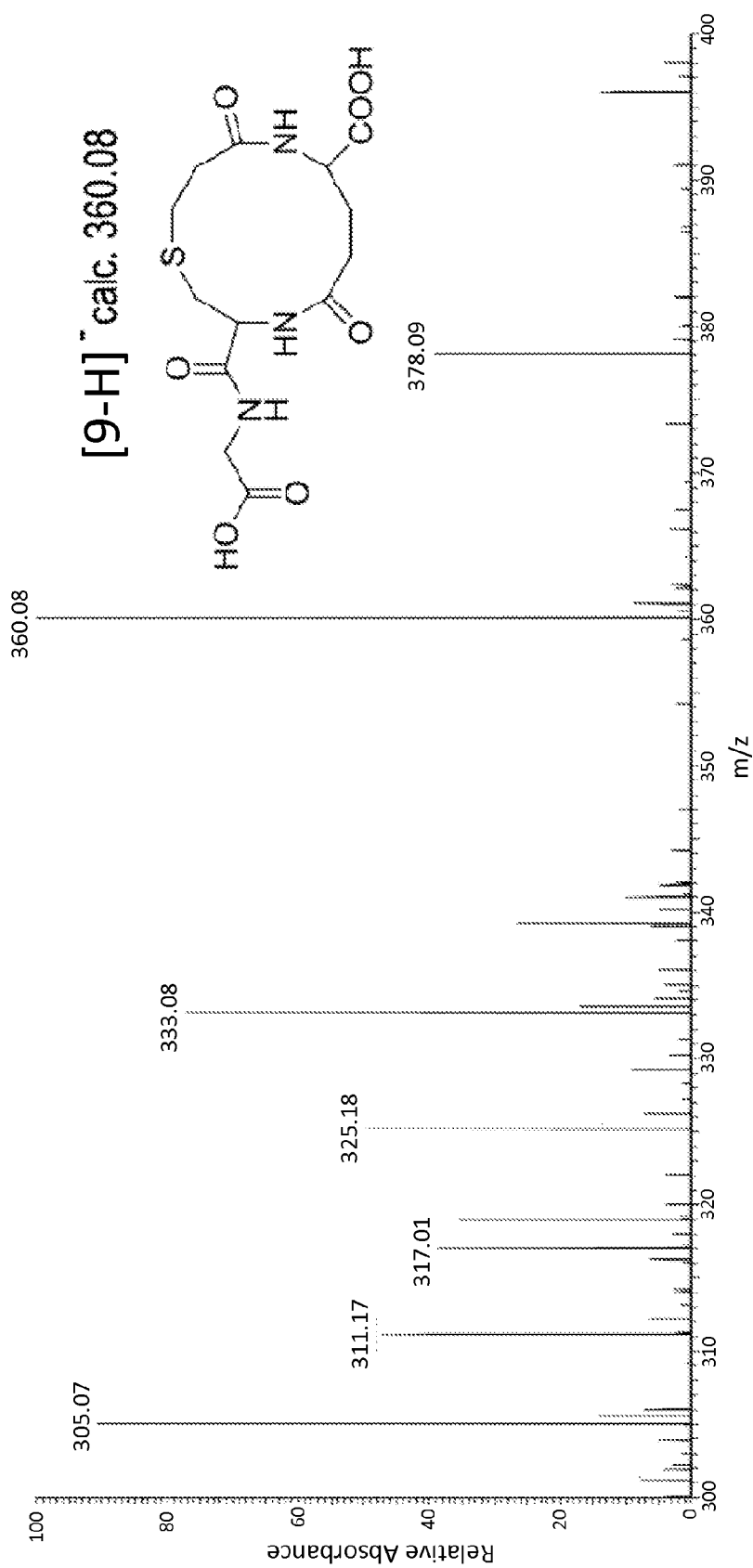
FIG. 1 is a high-resolution mass spectrum demonstrating formation of a 12-membered ring 9 when probe 8 is reacted with glutathione (GSH) in the presence of the surfactant cetyltrimethylammonium bromide (CTAB); the reaction time was 5 minutes. Background: negative; RT: 0.01; AV: 1; NL: 1.75E5; T: FTMS-pESI Full ms[300.00-400.00].
Figure 11:
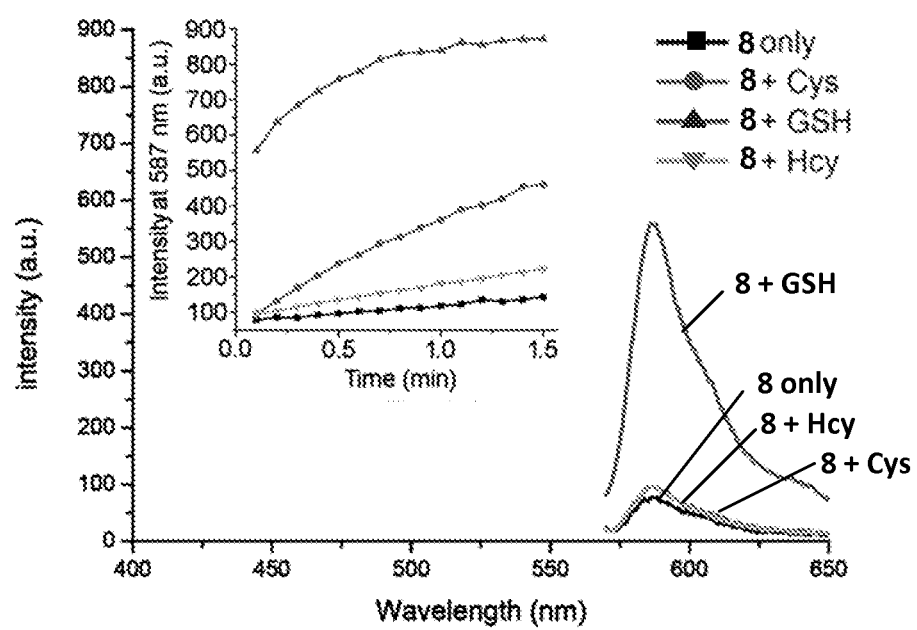
FIG. 11 shows fluorescence spectra ($\lambda_{ex}$=565 nm; $\lambda_{em}$=587 nm) obtained from the reaction of probe 8 with Cys, Hcy, GSH, and other amino acids in buffered 2.0 mM CTAB; selective detection of GSH resulted. Inset is a graph of fluorescence versus time.

Fluorescence spectra ($\lambda_{ex}$=565 nm; $\lambda_{em}$=587 nm) also were obtained immediately after addition of CTAB (FIG. 11). Significant fluorescence was obtained only with GSH. High resolution mass spectrometry confirmed formation of a 12-membered ring in the CTAB medium. A major peak corresponding to the ring was seen at m/z 360.08 (FIG. 1).

The reaction of probe 8 (2.5 μM) with 2 equivalents Cys, Hcy, or GSH in 2.0 mM CTAB buffered at pH 7.4 was monitored over time by fluorescence spectroscopy— $\lambda_{ex}$=565 nm; $\lambda_{em}$=587 nm. As shown in the inset of FIG. 11, immediate fluorescence was seen with GSH, and the fluorescence increased rapidly and reached a plateau in less than 2 minutes. In contrast, Cys and Hcy initially produced very little fluorescence; the fluorescence increased gradually over time, but remained much lower than the fluorescence obtained with GSH.

Example 6

Effect of Surfactants and Solvent on Probe 8 Selectivity

The thiol selectivity of probe 8 in the presence of various surfactants was evaluated. Probe 8 (2.5 μM) was combined with 2 equivalents of Cys, Hcy, or GSH in phosphate-buffered media (50 mM, pH=7.4) with a surfactant: (a) sodium dodecyl sulfate (SDS), 10 mM; (b) Triton® X-100, 0.3 mM; (c) benzyl-dimethyl-tridecyl-azanium chloride (benzalkonium chloride, BC), 0.05 mM, or (d) CTAB, 2 mM.

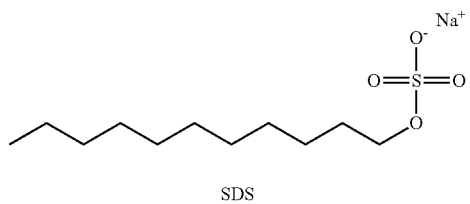

SDS

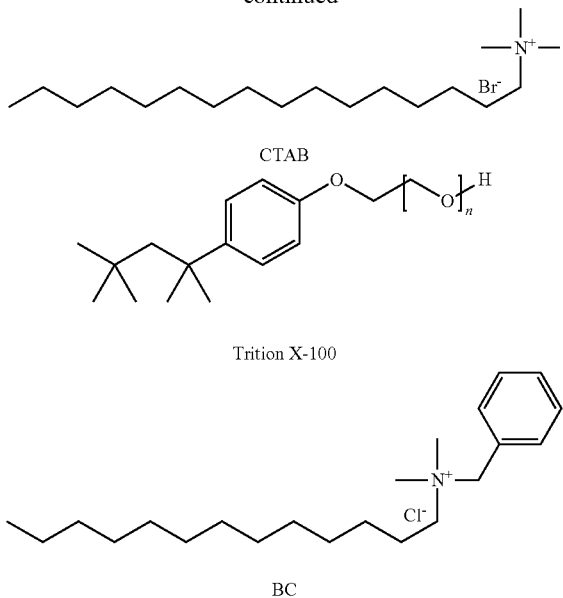

Figure 12:
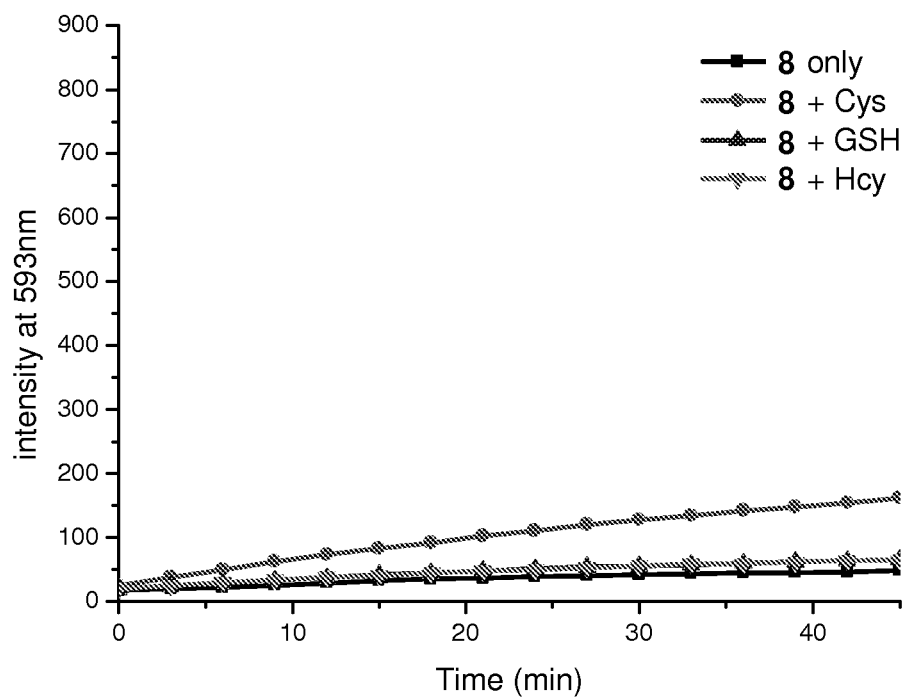
FIG. 12 is a graph illustrating the time-dependent change in fluorescence emission ($\lambda_{ex}/\lambda_{em}$=565/590 nm) when probe 8 was combined with Cys, Hcy, or GSH in phosphate-buffered media (50 mM, pH=7.4) including 10 mM sodium dodecylsulfate.
Figure 13:
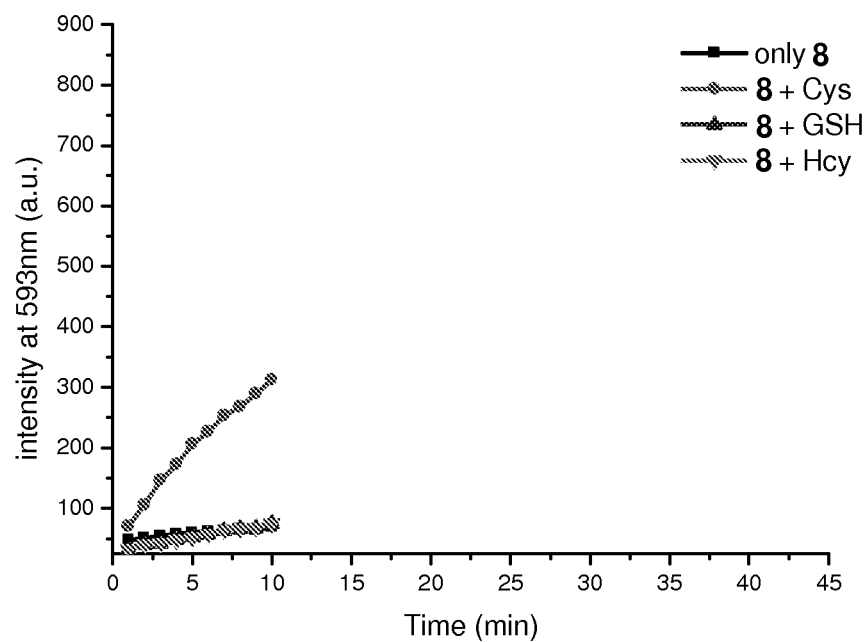
FIG. 13 is a graph illustrating the time-dependent change in fluorescence emission ($\lambda_{ex}/\lambda_{em}$=565/590 nm) when probe 8 was combined with Cys, Hcy, or GSH in phosphate-buffered media (50 mM, pH=7.4) including 0.3 mM Triton X-100.
Figure 14:
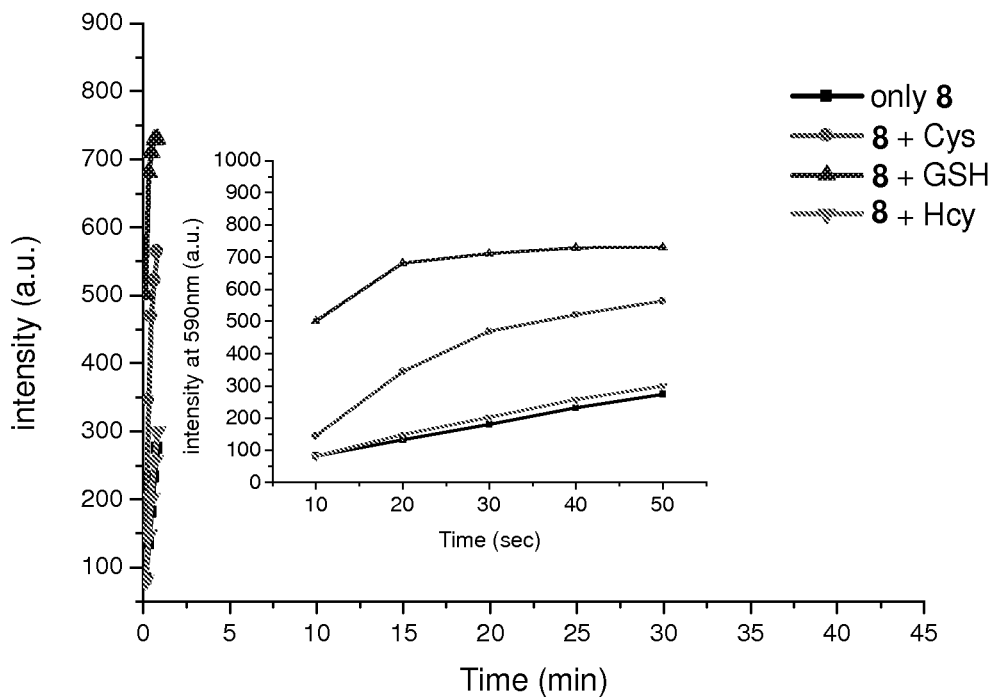
FIG. 14 is a graph illustrating the time-dependent change in fluorescence emission ($\lambda_{ex}/\lambda_{em}$=565/590 nm) when probe 8 was combined with Cys, Hcy, or GSH in phosphate-buffered media (50 mM, pH=7.4) including 0.05 mM benzyl-dimethyl-tridecyl-azanium chloride.
Figure 15:
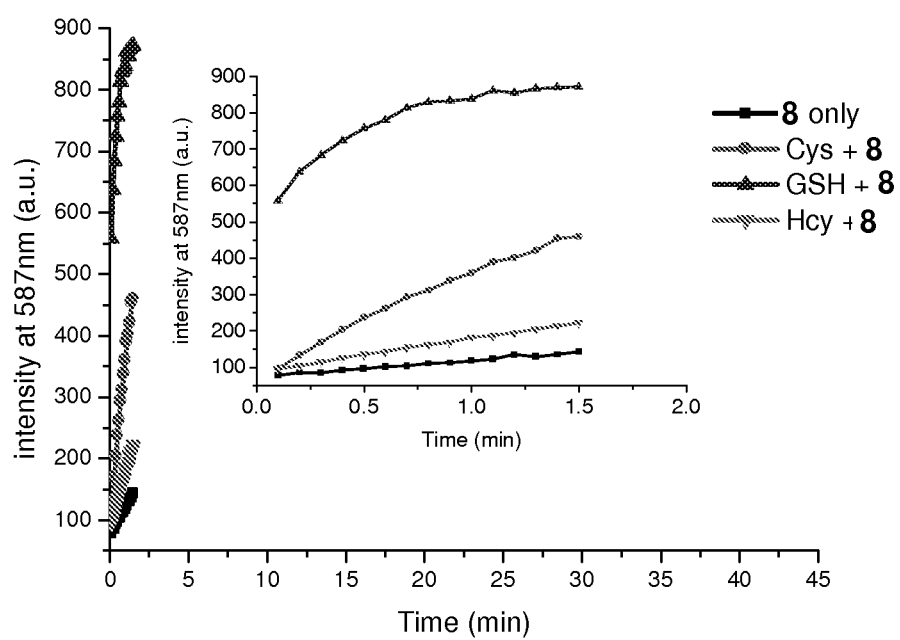
FIG. 15 is a graph illustrating the time-dependent change in fluorescence emission ($\lambda_{ex}/\lambda_{em}$=565/590 nm) when probe 8 was combined with Cys, Hcy, or GSH in phosphate-buffered media (50 mM, pH=7.4) including 2 mM CTAB.
Figure 16:
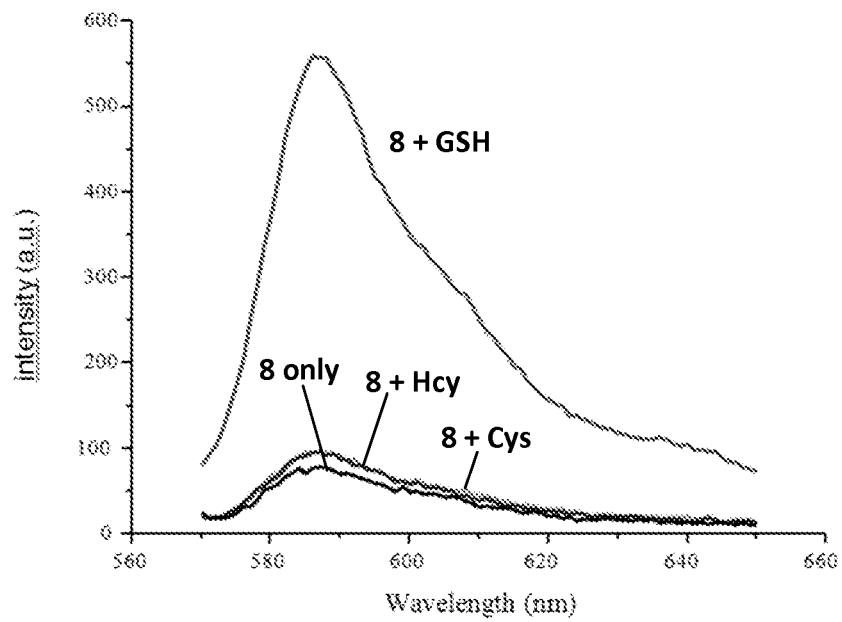
FIG. 16 shows fluorescence spectra ($\lambda_{ex}$=565 nm) obtained when probe 8 (2.5 µM) was combined with 2 equivalents of Cys, Hcy, or GSH is phosphate-buffered media (50 mM, pH=7.4) with 2 mM CTAB.

Time-dependent fluorescence changes ($\lambda_{ex}/\lambda_{em}$=565/590 nm) were monitored. The results are shown in FIGS. 12-15. As shown in FIGS. 12 and 13, Cys was preferentially detected by probe 8 in the presence of SDS and Triton X-100. In the presence of SDS (FIG. 12), fluorescence increased slowly over the measured timeframe of 50 minutes. In the presence of Triton® X-100 (FIG. 13), fluorescence increased much more quickly, and greater selectivity towards Cys was observed. When BC and CTAB were used, maximum fluorescence was achieved within 1-2 minutes. As seen in FIG. 14, both Cys and GSH were detected in the presence of BC, with GSH producing greater fluorescence. In the presence of CTAB (FIG. 15), much greater selectivity toward GSH was observed. FIGS. 16 and 17 are fluorescence spectra of probe 8 in the presence of CTAB (FIG. 16) and Triton X-100 (FIG. 17), again showing that probe 8 is selective for GSH in the presence of the cationic surfactant CTAB, but selective for Cys in the presence of Triton X-100.

The results show that probe 8 is an indicator for GSH in the presence of cationic surfactants such as BC and CTAB. Without wishing to be bound by any particular theory, favorable Coulombic attractions between cationic micelles and GSH may play a role in the selectivity of probe 8 towards GSH in the presence of cationic surfactants. Negatively-charged SDS suppressed the response of probe 8 towards all three thiols; while the non-ionic surfactant Triton X-100 enhanced the selectivity towards Cys and resulted in zero response for Hcy or GSH. The results with GSH are summarized in FIG. 18, which shows the fluorescence spectra obtained immediately upon addition of the surfactants. Inset is graph showing time-dependent fluorescence changes ($\lambda_{em}$=587 nm) of the same system.

In another assay, probe 8 (2.5 µM) was combined with 2 equivalents Cys, Hcy, GSH, leucine, proline, arginine, histidine, valine, methionine, threonine, glutamine, alanine, aspartic acid, norleucine, isoleucine, lysine, tryptophan, tyrosine, phenylalanine, cystine, or homocystine in 2.0 mM CTAB buffered at pH 7.4 (phosphate buffer, 50 mM). Fluorescence emission spectra ($\lambda_{ex}$=565 nm) were obtained immediately after addition of the thiols and other amino acids. As shown in FIG. 19, only GSH resulted in significant fluorescence. To further test the selectivity of probe 8 toward GSH, competition experiments were conducted with excess of other amino acids added to GSH, and no significant fluorescence intensity difference was observed in comparison to solutions containing GSH only.

Since surfactants can mimic organic environments, selectivity in DMSO:$H_2O$ (1:1, buffered at pH 7.4) was studied. Cys, Hcy, and GSH (2 equiv) were added to probe 8 (2.5 µM) in DMSO:$H_2O$ (1:1, buffered at pH 7.4), and fluorescence was measured over time. Selectivity of probe 8 toward GSH was demonstrated (FIG. 20).

The CTAB-mediated response of probe 8 towards GSH in the presence of Cys was evaluated. A mixture of Cys (2 µM) and increasing concentrations of GSH (0-2 µM) at pH 7.4 (phosphate buffer, 50 mM) were added to probe 8 (1.5 µM), and fluorescence spectra ($\lambda_{ex}$=565 nm) were obtained after 2 minutes. As shown in FIG. 21, there was no significant difference in the fluorescence spectrum of probe 8 when Cys was present. However, fluorescence increased greatly when GSH or GSH+Cys were reacted with probe 8. Thus, probe 8 is selective for GSH even in the presence of Cys. FIG. 22 shows a linear relationship between fluorescence intensity and GSH concentration with a correlation coefficient of 0.990, as well as a linear relationship with a mixture of GSH and Cys having a correlation coefficient of 0.9894.

The effect of GSH concentration was evaluated by combining various concentrations (0-6 µM) of GSH with probe 8 (2.5 µM) in 2.0 mM CTAB media buffered at pH 7.4 (phosphate buffer, 50 mM). The GSH concentrations were within the range of GSH in human plasma. FIG. 23 shows the fluorescence spectra ($\lambda_{ex}$=565 nm) obtained immediately upon addition of CTAB. FIG. 23 inset is a graph illustrating submicromolar sensitivity and a linear relationship (correlation coefficient of 0.998) between fluorescence intensity ($\lambda_{ex}$=565 nm, $\lambda_{em}$=587 nm) and GSH concentration. Measurements were taken immediately after addition of CTAB. These results demonstrate that the probe 8-CTAB system functions well within the range of typical GSH concentrations in human plasma.

Example 7

Effect of pH on GSH Detection with Probe 8

While the probe 8-CTAB-GSH signal was high at pH 7.4 (see, e.g., Example 6), it is known that acrylate esters are susceptible to hydrolysis at high pH and that GSH is also relatively unstable under the same conditions (half-life of 9 hours at pH 7.4 compared to 16 hours at pH 6.5; Stevens et al., *Biochem. Educ.*, 1983, 11, 70).

The spectral behavior of the probe 8-CTAB system was investigated over a wide range of pH values (pH 5.5 to pH 8), and its response to the various thiols was studied at lower pH values. Probe 8 (2.5 µM) was added to CTAB media (2 mM) buffered at pH 5.5 to 8, and the absorbance was monitored over time at a wavelength of 580 nm (FIG. 24). Probe 8 showed the greatest background signal at the higher pH values investigated. The probe 8-CTAB system was most stable at lower pH values. The absorbance spectra of probe 8 in CTAB media at pH 6.0, 7.0, and 8.0 after 1 minute and 10 minutes are shown in FIGS. 25 and 26, respectively.

The reaction with thiols at pH 6 was evaluated. Absorption spectra of probe 8 (2.5 µM) upon addition of thiols (2 equivalents) in 2.0 mM CTAB media buffered at pH 6 (phosphate buffer, 50 mM) were obtained after 20 minutes (FIG. 27). Fluorescence spectra ($\lambda_{ex}$=565 nm) also were obtained (FIG. 28). The inset in FIG. 28 shows the time-dependent fluorescence changes ($\lambda_{em}$=587 nm); the fluorescence increase was slightly less rapid as compared to pH 7.4 (see, e.g., FIG. 15); however, the selectivity towards GSH was further enhanced through the complete elimination of any residual Cys and Hcy response. Thus pH 6 was chosen for further application studies in plasma.

Example 8

Detection of GSH in Plasma with Probes 5 and 8

Human plasma (0.5 mL) was reduced using HCl (0.2 M, 40 μL) in the presence of triphenylphosphine (0.1 M, 80 μL) as a catalyst for 15 minutes at room temperature. Proteins present in the sample after reduction were precipitated by addition of acetonitrile (0.5 mL), followed by centrifugation (4000 rpm) of the sample for 20 minutes. The supernatant liquid was then added to a solution of probe 5 (10 μM) in pH 7.4 HEPES buffer solution (0.1 M, 5 mL) in the presence of 1.0 mM CTAB. Fluorescence spectra ($\lambda_{ex}$=550 nm) were obtained after 25 minutes.

As shown in FIG. 29, the fluorescence emission showed a significant increase with addition of reduced plasma. However, the fluorescence emission of solutions including probe 5 showed no obvious fluorescence increase when controls of either triphenylphosphine alone or deproteinized plasma (without reducing agent) were added, demonstrating that the fluorescence increase was due to the reaction of probe 5 with Cys. The amount of Cys in the plasma sample as determined by the standard addition method to be 172.8±8.7 μM (n=3), which is well within the reported Cys concentration range (135.8-266.5 μM) for human plasma samples from healthy individuals. The results demonstrate that probe 5 may be useful for quantitative detection of Cys in biological samples.

Plasma proteins were precipitated using MeCN (two thirds of the reconstitution volume) and removed by centrifugation at 4,000 rpm for 30 min. The supernatant liquid was diluted to provide 10% deproteinized plasma, and added to a solution of probe 8 (1-1.5 μM) in phosphate buffer (pH 6, 50 mM) in the presence of 2.0 mM CTAB. Some samples were spiked with GSH (0-2.0 μM) or a mixture of GSH (2 μM) and Cys (2 μM).

The fluorescence response of replicate (n=3) samples and GSH-spiked samples were monitored as above and the GSH content in the plasma sample was determined from the regression equation of a standard calibration curve (FIG. 30, probe 8=1 μM). Measurements were taken 8 minutes after mixing. Fluorescence emission spectra ($\lambda$ex=565 nm) also were obtained 8 minutes after mixing (FIG. 31. probe 8=1 μM). Using the calibration curve, the GSH content of the plasma sample was determined to be 3.24±0.14 μM, which is well within the reported GSH concentration range for human plasma samples from healthy individuals. Recoveries of the known spiked amounts of GSH were between 99.2% and 102.3% with a satisfactory precision (Table 1). As shown in Table 1, the relative standard deviation for 3 replicate samples was less than 6%. These results revealed the potential applicability and reliability of using probe 8 in quantitative detection of GSH in human plasma.

Sensitivity and selectivity were evaluated by obtaining fluorescence spectra of plasma alone, plasma+0.5 μM GSH, plasma+2 μM GSH, and plasma+2 μM GSH and 2 μM Cys (probe 8=1.5 μM). Measurements were taken 8 minutes after mixing. The results are shown in FIG. 32. Notably, addition of Cys did not exhibit significant interference with the GSH determination.

TABLE 1

Determination of GSH content in 10% deproteinized human plasma samples.

| Sample | GSH Spiked (μM) | GSH Measured (μM) | Recovery (%) | RSD (%) |
|---|---|---|---|---|
| 10% Plasma | 0 | 0.324 | — | 4.42 |
| 10% Plasma + GSH | 0.3 | 0.631 | 102.3 | 4.90 |
| 10% Plasma + GSH | 0.6 | 0.919 | 99.2 | 4.24 |
| 10% Plasma + GSH | 0.9 | 1.224 | 100.0 | 5.88 |

Example 9

Selective Detection of GSH in Dried Blood Spots with Probe 8

Pig blood (10, 20, and 40 μL) was spotted on Whatman 903™ filter paper, and dried at room temperature for 3-4 hours. Oxidized glutathione was extracted from the dried blood spot (DBS) with 2.5 mL phosphate buffer (100 mM, pH 7.4). The extract was reduced with TCEP (tris-(2-carboxyethyl)-phosphine) (35 mM) to reduce disulfides. Reduced GSH was isolated by gel filtration of the reduced extract on a PD-10 desalting column (Sephadex® G-25 (cross-linked dextran gel), GE Healthcare) using phosphate buffer (100 mM, pH 7.4) as eluent. Fractions of about 1.5-2.5 mL were collected in 4 mL vials. CTAB (2.0 mM) and probe 8 (2.5 μM) were added to the vials. The solution was buffered at pH 6.0 (phosphate buffer, 50 mM).

GSH was detected in the fourth and fifth eluted fractions by development of a pink color after addition of CTAB and probe 8. Absorption and fluorescence spectra ($\lambda$ex=565 nm) were obtained from the fifth fraction (FIGS. 33 and 34, respectively). Measurements were taken immediately after mixing. FIG. 33 is a fluorescence spectrum demonstrating that probe 8 detected GSH in the extract obtained 10 μL dried pig blood.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound having a chemical structure according to general formula I:

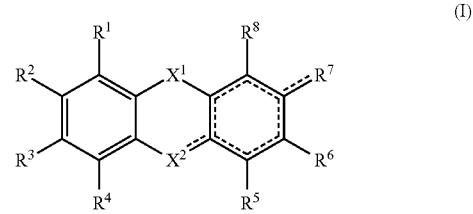

(I)

where each bond depicted as "- - - - - -" is a single or double bond as needed to satisfy valence requirements;

$R^1$, $R^3$-$R^6$ and $R^8$ independently are H, hydroxyl, thiol, lower alkyl, carboxyalkyl, amino, alkoxy, or halogen;

$R^2$ is an α,β-unsaturated aliphatic ester;

$R^7$ is O, S, H, hydroxyl, thiol, lower alkyl, carboxyalkyl, amino, alkoxy, or halogen, or $R^7$ and $R^8$ together form a cycloalkyl or aryl ring;

$X^1$ is $CH_2$, S, NH, O, Se, $Si(CH_3)_2$, $Ge(CH_3)_2$, $Sn(CH_3)_2$, or $C(CH_3)_2$; and $X^2$ is CH, $CH_2$, N, NH, or $CR^9$ where $R^9$ is aryl, wherein
when $X^1$ is O, then $R^2$ is an acrylate ester, $X^2$ is CH or N, $R^7$ is O, and $R^1$, $R^3$-$R^6$, and $R^8$ independently are H or lower alkyl, or
when $X^1$ is O or S, then $R^7$ and $R^8$ together form an aryl ring.

2. The compound of claim 1 where $X^1$ is O or S, and $R^1$ and $R^3$-$R^6$ independently are H or lower alkyl.

3. The compound of claim 1 where $X^1$ is O, $R^7$ and $R^8$ together form an aryl ring, $X^2$ is N or $CR^9$, $R^1$ is lower alkyl or H, $R^2$ is an acrylate ester, and $R^3$-$R^6$ are H.

4. The compound of claim 1 having the structure:

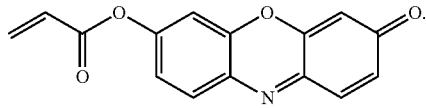 [SMILES: C=CC(=O)Oc1ccc2nc3ccc(=O)cc-3oc2c1]

5. A kit for detecting at least one compound comprising a thiol group and an amino group, comprising at least one probe according to claim 1.

6. The kit of claim 5 where the probe is

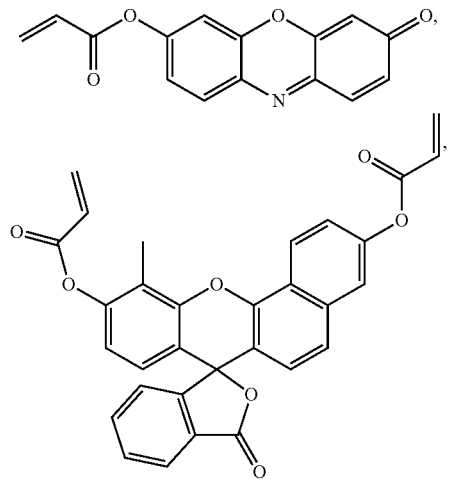

or a combination thereof.

7. A compound having a chemical structure according to general formula II:

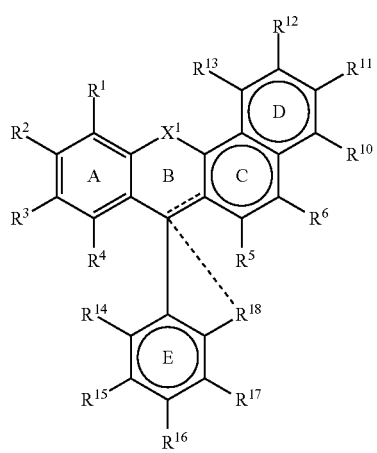

where " ----- " indicates a single or double bond as needed to satisfy valence requirements and "------" indicates an optional single bond;

$R^1$, $R^3$-$R^6$ and $R^8$ independently are H, hydroxyl, thiol, lower alkyl, carboxyalkyl, amino, alkoxy, or halogen;

$X^1$ is $CH_2$, S, NH, O, Se, $Si(CH_3)_2$, $Ge(CH_3)_2$, $Sn(CH_3)_2$, or $C(CH_3)_2$;

$R^2$ and $R^{11}$ independently are an α,β-unsaturated aliphatic ester;

$R^{10}$, $R^{12}$, and $R^{13}$ independently are H, hydroxyl, thiol, lower alkyl, carboxyalkyl, amino, alkoxy, or halogen;

$R^{14}$-$R^{17}$ independently are H, alkyl, acyl, carboxyl, nitro, amino, alkyl amino, or —$SO_3H$; and $R^{18}$ is H, hydroxyl, lower alkyl, lower alkoxy, —$SO_3H$ or —$COOR^{19}$ where $R^{19}$ is H or lower alkyl and the bond depicted as " ----- " in ring B is a double bond, or $R^{18}$ is one or more atoms forming a ring system with rings B and E and the bond depicted as " ----- " in ring B is a single bond.

8. The compound of claim 7 where each of $R^2$ and $R^{11}$ is an acrylate ester, and $R^{18}$ is —COOH or $R^{18}$ is —C(O)O— and forms a ring system with rings B and E.

9. The compound of claim 8 where $R^1$, $R^3$-$R^6$, $R^{10}$ and $R^{12}$-$R^{17}$ independently are H or lower alkyl.

10. The compound of claim 9 where $X^1$ is O.

11. The compound of claim 7 having the structure:

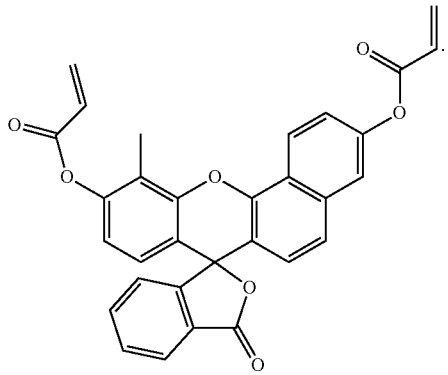 [SMILES: C=CC(=O)Oc1ccc2c3c(ccc2c1)C1(OC(=O)c2ccccc21)c1ccc(OC(=O)C=C)c(C)c1O3]

12. A method for selectively detecting a compound comprising a thiol group and an amino group, comprising:
combining a sample potentially comprising at least one compound comprising a thiol group and an amino group with a solution comprising a probe having a structure according to claim 1 to produce a reaction mixture;
allowing a reaction between the sample and the probe to proceed for an effective period of time to produce a detectable change in the reaction mixture's absorbance spectrum, emission spectrum, or both, where the change indicates that the compound is present; and
detecting the change.

13. The method of claim 12 where the sample comprises blood, a blood product, a blood component, urine, a urine product, or a urine component.

14. The method of claim 13, further comprising:
obtaining plasma;
reducing the plasma by addition of a reducing agent;
precipitating proteins in the plasma;
separating precipitated proteins from the plasma to form the sample; and
subsequently combining the sample with the solution comprising the probe.

15. The method of claim 13, further comprising:
obtaining a dried blood spot prepared by spotting whole blood onto an absorbent material and allowing the blood to dry;
extracting the dried blood spot with a solvent to produce an extract;
reducing the extract by addition of a reducing agent to form a reduced extract;
fractionating the reduced extract to obtain the sample; and subsequently combining the sample with the solution comprising the probe.

16. The method of claim 12 where detecting the change comprises (i) comparing a color of the reaction mixture before the reaction to a color of the reaction mixture after the reaction, (ii) detecting a change in absorbance of the reaction mixture at one or more wavelengths after the reaction has proceeded for the effective period of time, (iii) comparing an absorbance spectrum of the reaction mixture at a first time after combining the sample and the probe to an absorbance spectrum of the reaction mixture after the reaction has proceeded for the effective period of time, (iv) detecting a change in emission of the reaction mixture at one or more wavelengths after the reaction has proceeded for the effective period of time, (v) comparing an emission spectrum of the reaction mixture at a first time after combining the sample and the probe to an emission spectrum of the solution after the reaction has proceeded for the effective period of time, or (vi) any combination thereof.

17. The method of claim 12 where the probe is

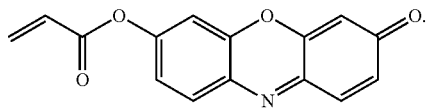 [SMILES: C=CC(=O)Oc1ccc2nc3ccc(=O)cc-3oc2c1]

18. The method of claim 17 where the at least one compound is glutathione, and the reaction mixture further comprises a cationic surfactant.

19. The method of claim 12 where the at least one compound is cysteine, and the probe is

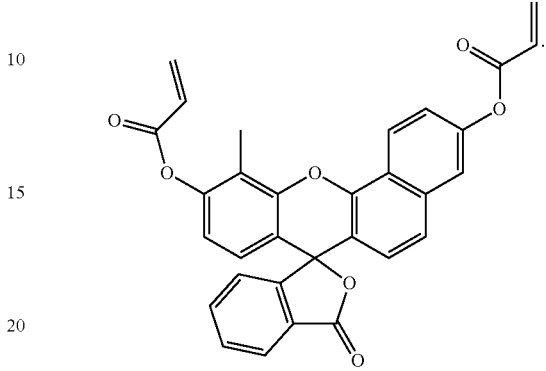

20. The method of claim 19 where the reaction mixture further comprises a cationic surfactant.

* * * * *